(12) United States Patent
Wang et al.

(10) Patent No.: US 10,704,092 B2
(45) Date of Patent: Jul. 7, 2020

(54) DETECTION METHODS BASED ON SEQUENCING

(71) Applicants: CapitalBio Corporation, Beijing (CN); Tsinghua University, Beijing (CN)

(72) Inventors: Dong Wang, Beijing (CN); Hui Wang, Beijing (CN); Yan Zhang, Beijing (CN); Guangxin Xiang, Beijing (CN); Yimin Sun, Beijing (CN); Wanli Xing, Beijing (CN); Jing Cheng, Beijing (CN)

(73) Assignees: CAPITALBIO CORPORATION, Beijing (CN); TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 15/525,037

(22) PCT Filed: Nov. 10, 2015

(86) PCT No.: PCT/CN2015/000784
§ 371 (c)(1),
(2) Date: May 5, 2017

(87) PCT Pub. No.: WO2016/074338
PCT Pub. Date: May 19, 2016

(65) Prior Publication Data
US 2019/0085393 A1 Mar. 21, 2019

(30) Foreign Application Priority Data

Nov. 10, 2014 (CN) .......................... 2014 1 0643497

(51) Int. Cl.
| | |
|---|---|
| *C12Q 1/6876* | (2018.01) |
| *C12Q 1/6827* | (2018.01) |
| *C12Q 1/6858* | (2018.01) |
| *C12Q 1/6883* | (2018.01) |
| *C12Q 1/6853* | (2018.01) |
| *C12Q 1/6869* | (2018.01) |

(52) U.S. Cl.
CPC ......... *C12Q 1/6876* (2013.01); *C12Q 1/6827* (2013.01); *C12Q 1/6853* (2013.01); *C12Q 1/6858* (2013.01); *C12Q 1/6869* (2013.01); *C12Q 1/6883* (2013.01); *C12Q 2600/156* (2013.01); *C12Q 2600/16* (2013.01)

(58) Field of Classification Search
CPC ..... C12Q 1/6876; C12Q 1/6827; C07H 21/04
See application file for complete search history.

(56) References Cited

U.S. PATENT DOCUMENTS

| | | | | |
|---|---|---|---|---|
| 2010/0041563 | A1* | 2/2010 | Li ................ | C12Q 1/6858 506/9 |
| 2011/0003301 | A1* | 1/2011 | Raymond ........... | C12Q 1/686 435/6.11 |
| 2013/0261003 | A1* | 10/2013 | Oliphant ............ | C12Q 1/6809 506/2 |

FOREIGN PATENT DOCUMENTS

| | | |
|---|---|---|
| CN | 1177938 C | 12/2004 |
| CN | 101275904 A | 10/2008 |
| CN | 102181443 A | 9/2011 |
| CN | 103194534 A | 7/2013 |
| CN | 104372093 A | 2/2015 |
| WO | 2005118847 A1 | 12/2005 |
| WO | WO 2012/055069 * | 5/2012 |
| WO | 2013009175 A1 | 1/2013 |

OTHER PUBLICATIONS

Deshpande et al, A rapid multiplex assay for nucleic acid-based diagnostics, Journal of Microbiological Methods, 2010, 80, 155-163. (Year: 2010).*
SEQ ID No. 7 search results from STIC, printed on Jun. 15, 2019, pp. 1-11 (Year: 2019).*
SEQ ID No. 8 search results from STIC, printed on Jun. 13, 2019, pp. 1-11 (Year: 2019).*
SEQ ID No. 9 search results from STIC, printed on Jun. 13, 2019, pp. 1-11 (Year: 2019).*
SEQ ID No. 10 search results from STIC, printed on Jun. 13, 2019, pp. 1-11 (Year: 2019).*
SEQ ID No. 11 search results from STIC, printed on Jun. 14, 2019, pp. 1-11 (Year: 2019).*
SEQ ID No. 12 search results from STIC, printed on Jun. 13, 2019, pp. 1-11 (Year: 2019).*
SEQ ID No. 13 search results from STIC, printed on Jun. 14, 2019, pp. 1-11 (Year: 2019).*
SEQ ID No. 14 search results from STIC, printed on Jun. 14, 2019, pp. 1-11 (Year: 2019).*
SEQ ID No. 15 search results from STIC, printed on Jun. 14, 2019, pp. 1-11 (Year: 2019).*
SEQ ID No. 16 search results from STIC, printed on Jun. 13, 2019, pp. 1-11 (Year: 2019).*
SEQ ID No. 17 search results from STIC, printed on Jun. 14, 2019, pp. 1-11 (Year: 2019).*
SEQ ID No. 18 search results from STIC, printed on Jun. 14, 2019, pp. 1-11 (Year: 2019).*

(Continued)

*Primary Examiner* — Narayan K Bhat
(74) *Attorney, Agent, or Firm* — Rimon, P.C.

(57) ABSTRACT

Provided herein is a multi-sample and multi-locus method for analyzing a genetic locus. In particular, provided herein is a method for SNP detection and analysis based on high-throughput sequencing, comprising designing a probe, pre-amplification and biotin labeling, hybridization, ligation, barcode specific primer extension, sequencing and analyzing the SNP locus. A probe set is for the analysis is also provided.

41 Claims, 11 Drawing Sheets

Specification includes a Sequence Listing.

(56) References Cited

OTHER PUBLICATIONS

SEQ ID No. 19 search results from STIC, printed on Jun. 13, 2019, pp. 1-10 (Year: 2019).*
SEQ ID No. 20 search results from STIC, printed on Jun. 14, 2019, pp. 1-12 (Year: 2019).*
SEQ ID No. 21 search results from STIC, printed on Jun. 14, 2019, pp. 1-11 (Year: 2019).*
SEQ ID No. 22 search results from STIC, printed on Jun. 13, 2019, pp. 1-11 (Year: 2019).*
SEQ ID No. 23 search results from STIC, printed on Jun. 13, 2019, pp. 1-11 (Year: 2019).*
SEQ ID No. 24 search results from STIC, printed on Jun. 13, 2019, pp. 1-11 (Year: 2019).*
SEQ ID No. 25 search results from STIC, printed on Jun. 14, 2019, pp. 1-11 (Year: 2019).*
SEQ ID No. 26 search results from STIC, printed on Jun. 13, 2019, pp. 1-14 (Year: 2019).*
SEQ ID No. 27 search results from STIC, printed on Jun. 13, 2019, pp. 1-11 (Year: 2019).*
SEQ ID No. 28 search results from STIC, printed on Jun. 13, 2019, pp. 1-10 (Year: 2019).*
SEQ ID No. 29 search results from STIC, printed on Jun. 13, 2019, pp. 1-10 (Year: 2019).*
SEQ ID No. 30 search results from STIC, printed on Jun. 13, 2019, pp. 1-13 (Year: 2019).*
SEQ ID No. 31 search results from STIC, printed on Jun. 13, 2019, pp. 1-10 (Year: 2019).*
SEQ ID No. 32 search results from STIC, printed on Jun. 13, 2019, pp. 1-11 (Year: 2019).*
SEQ ID No. 33 search results from STIC, printed on Jun. 13, 2019, pp. 1-12 (Year: 2019).*
European Patent Office, European Search Opinion for application EP15859614, dated May 16, 2018, 3 pages.
European Patent Office, Supplementary European Search Report for application EP15859614, dated May 2, 2018, 2 pages.
PCT, International Preliminary Report on Patentability for application PCT/CN2015/000784, dated May 16, 2017, 7 pages.
Wan Du et al. "Associations between GJB2, Mitochondrial 12S rRNA, SLC26A4 Mutations, and Hearing Loss among Three Ethnicaities", Biomed Research International, vol. 2014, Jan. 1, 2014, pp. 1-6, XP055471833, ISSN: 2314-6133, DOI: 10.1155/2014/746838.
CN, First Office Action for CN patent application 201410643497, dated Jan. 6, 2016, 10 pages.
JP, Request for Examination for JP patent application 2017-525077, dated Oct. 18, 2018, 1 page.
JP, Amendment for JP patent application 2017-525077, dated Oct. 18, 2018, 4 pages with additional 5 pages of English translation.
EP, Response to office action for EP patent application 15859614, dated Dec. 14, 2018, 14 pages.
EP, Office Action for EP patent application 15859614, dated Feb. 11, 2019, 4 pages.
Refusal Reason Notice for Japanese patent application JP2017-525077, dated Nov. 19, 2019, 8 pages with extra 8 pages of English language equivalent or summary.
Response to Examination Report for European patent application EP15859614.8, dated Jul. 10, 2019, 4 pages.
Claims marked-up for Response to Examination Report for European patent application EP15859614.8, dated Jul. 10, 2019, 4 pages.
Description marked-up for Response to Examination Report for European patent application EP15859614.8, dated Jul. 10, 2019, 4 pages.
Communication under Rule 71(3) EPC for European patent application EP15859614.8, dated Sep. 30, 2019, 64 pages.
Smith, Richard J.H. et al.,"Deafness and Hereditary Hearing Loss Overview," GeneReviewsR—NCBI Bookshelf, [online], Oct. 12, 2014, [Nov. 13, 2019 Index], https://web.archive.org/web/20141012031625/https://www.ncbi.nlm.nih.gov/books/NBK-1434/>, 24 pages.

* cited by examiner

SEQUENCE LISTING

<160> NUMBER OF SEQ ID NOS: 33

<210> SEQ ID NO 1
<211> LENGTH: 21
<212> TYPE: DNA
<213> ORGANISM: Artificial Sequences
<220> FEATURE:
<223> OTHER INFORMATION: Synthetic

<400> SEQUENCE: 1
ccagactcag agaagtctcc c                                      21

<210> SEQ ID NO 2
<211> LENGTH: 21
<212> TYPE: DNA
<213> ORGANISM: Artificial Sequences
<220> FEATURE:
<223> OTHER INFORMATION: Synthetic

<400> SEQUENCE: 2
atgctagcga ctgagccttg a                                      21

<210> SEQ ID NO 3
<211> LENGTH: 20
<212> TYPE: DNA
<213> ORGANISM: Artificial Sequences
<220> FEATURE:
<223> OTHER INFORMATION: Synthetic

<400> SEQUENCE: 3
cgtgtagcag caggaagtat                                        20

```
<210> SEQ ID NO 4
<211> LENGTH: 20
<212> TYPE: DNA
<213> ORGANISM: Artificial Sequences
<220> FEATURE:
<223> OTHER INFORMATION: Synthetic

<400> SEQUENCE: 4
aagaggaaca ccacactcac                                              20

<210> SEQ ID NO 5
<211> LENGTH: 20
<212> TYPE: DNA
<213> ORGANISM: Artificial Sequences
<220> FEATURE:
<223> OTHER INFORMATION: Synthetic

<400> SEQUENCE: 5
tggctaaggt tgtctggtag                                              20

<210> SEQ ID NO 6
<211> LENGTH: 20
<212> TYPE: DNA
<213> ORGANISM: Artificial Sequences
<220> FEATURE:
<223> OTHER INFORMATION: Synthetic

<400> SEQUENCE: 6
ccctgatgaa ggctacaaag                                              20

<210> SEQ ID NO 7
<211> LENGTH: 37
<212> TYPE: DNA
<213> ORGANISM: Artificial Sequences
<220> FEATURE:
<223> OTHER INFORMATION: Synthetic

<400> SEQUENCE: 7
acacgacgct cttccgatct agtagcaatt atcgtct                           37

<210> SEQ ID NO 8
<211> LENGTH: 37
<212> TYPE: DNA
<213> ORGANISM: Artificial Sequences
<220> FEATURE:
<223> OTHER INFORMATION: Synthetic

<400> SEQUENCE: 8
acacgacgct cttccgatct agtagcaatt atcgtca                           37

<210> SEQ ID NO 9
<211> LENGTH: 37
<212> TYPE: DNA
<213> ORGANISM: Artificial Sequences
<220> FEATURE:
<223> OTHER INFORMATION: Synthetic

<400> SEQUENCE: 9
acacgacgct cttccgatct agtagcaatt atcgtcg                           37

<210> SEQ ID NO 10
<211> LENGTH: 37
<212> TYPE: DNA
<213> ORGANISM: Artificial Sequences
<220> FEATURE:
<223> OTHER INFORMATION: Synthetic
```

```
<400> SEQUENCE: 10
acacgacgct cttccgatct agtagcaatt atcgtcc                              37

<210> SEQ ID NO 11
<211> LENGTH: 41
<212> TYPE: DNA
<213> ORGANISM: Artificial Sequences
<220> FEATURE:
<223> OTHER INFORMATION: Synthetic

<400> SEQUENCE: 11
gaaataaaac aaaagatgtt agatcggaag agcacacgtc t                         41

<210> SEQ ID NO 12
<211> LENGTH: 40
<212> TYPE: DNA
<213> ORGANISM: Artificial Sequences
<220> FEATURE:
<223> OTHER INFORMATION: Synthetic

<400> SEQUENCE: 12
acacgacgct cttccgatct ccaggctgca agaacgtgtg                           40

<210> SEQ ID NO 13
<211> LENGTH: 39
<212> TYPE: DNA
<213> ORGANISM: Artificial Sequences
<220> FEATURE:
<223> OTHER INFORMATION: Synthetic

<400> SEQUENCE: 13
acacgacgct cttccgatct tgcaacaccc tgcagccag                            39

<210> SEQ ID NO 14
<211> LENGTH: 40
<212> TYPE: DNA
<213> ORGANISM: Artificial Sequences
<220> FEATURE:
<223> OTHER INFORMATION: Synthetic

<400> SEQUENCE: 14
ctacgatcac tacttcccca gatcggaaga gcacacgtct                           40

<210> SEQ ID NO 15
<211> LENGTH: 37
<212> TYPE: DNA
<213> ORGANISM: Artificial Sequences
<220> FEATURE:
<223> OTHER INFORMATION: Synthetic

<400> SEQUENCE: 15
acacgacgct cttccgatct acatccggct atgggcc                              37

<210> SEQ ID NO 16
<211> LENGTH: 37
<212> TYPE: DNA
<213> ORGANISM: Artificial Sequences
<220> FEATURE:
<223> OTHER INFORMATION: Synthetic

<400> SEQUENCE: 16
acacgacgct cttccgatct cacatccggc tatgggc                              37
```

```
<210> SEQ ID NO 17
<211> LENGTH: 40
<212> TYPE: DNA
<213> ORGANISM: Artificial Sequences
<220> FEATURE:
<223> OTHER INFORMATION: Synthetic

<400> SEQUENCE: 17
ctgcagctga tcttcgtgtc gatcggaaga gcacacgtct                    40

<210> SEQ ID NO 18
<211> LENGTH: 37
<212> TYPE: DNA
<213> ORGANISM: Artificial Sequences
<220> FEATURE:
<223> OTHER INFORMATION: Synthetic

<400> SEQUENCE: 18
acacgacgct cttccgatct tggcctaccg gagacat                       37

<210> SEQ ID NO 19
<211> LENGTH: 37
<212> TYPE: DNA
<213> ORGANISM: Artificial Sequences
<220> FEATURE:
<223> OTHER INFORMATION: Synthetic

<400> SEQUENCE: 19
acacgacgct cttccgatct cgtggcctac cggagac                       37

<210> SEQ ID NO 20
<211> LENGTH: 40
<212> TYPE: DNA
<213> ORGANISM: Artificial Sequences
<220> FEATURE:
<223> OTHER INFORMATION: Synthetic

<400> SEQUENCE: 20
gagaagaaga ggaagttcat gatcggaaga gcacacgtct                    40

<210> SEQ ID NO 21
<211> LENGTH: 33
<212> TYPE: DNA
<213> ORGANISM: Artificial Sequences
<220> FEATURE:
<223> OTHER INFORMATION: Synthetic

<400> SEQUENCE: 21
acacgacgct cttccgatct accggccgtc acg                           33

<210> SEQ ID NO 22
<211> LENGTH: 33
<212> TYPE: DNA
<213> ORGANISM: Artificial Sequences
<220> FEATURE:
<223> OTHER INFORMATION: Synthetic

<400> SEQUENCE: 22
acacgacgct cttccgatct accggccgtc acc                           33

<210> SEQ ID NO 23
<211> LENGTH: 33
<212> TYPE: DNA
<213> ORGANISM: Artificial Sequences
<220> FEATURE:
<223> OTHER INFORMATION: Synthetic
```

-continued

<400> SEQUENCE: 23
acacgacgct cttccgatct accggccgtc aca                          33

<210> SEQ ID NO 24
<211> LENGTH: 33
<212> TYPE: DNA
<213> ORGANISM: Artificial Sequences
<220> FEATURE:
<223> OTHER INFORMATION: Synthetic

<400> SEQUENCE: 24
acacgacgct cttccgatct accggccgtc act                          33

<210> SEQ ID NO 25
<211> LENGTH: 40
<212> TYPE: DNA
<213> ORGANISM: Artificial Sequences
<220> FEATURE:
<223> OTHER INFORMATION: Synthetic

<400> SEQUENCE: 25
ctcctcaagt atacttcaaa gatcggaaga gcacacgtct                   40

<210> SEQ ID NO 26
<211> LENGTH: 21
<212> TYPE: DNA
<213> ORGANISM: Artificial Sequences
<220> FEATURE:
<223> OTHER INFORMATION: Synthetic

<400> SEQUENCE: 26
agtgcttagt tgaacagggc c                                       21

<210> SEQ ID NO 27
<211> LENGTH: 21
<212> TYPE: DNA
<213> ORGANISM: Artificial Sequences
<220> FEATURE:
<223> OTHER INFORMATION: Synthetic

<400> SEQUENCE: 27
ggttcgtcca agtgcacttt c                                       21

<210> SEQ ID NO 28
<211> LENGTH: 21
<212> TYPE: DNA
<213> ORGANISM: Artificial Sequences
<220> FEATURE:
<223> OTHER INFORMATION: Synthetic

<400> SEQUENCE: 28
aaaggaggtg tggggagatg a                                       21

<210> SEQ ID NO 29
<211> LENGTH: 22
<212> TYPE: DNA
<213> ORGANISM: Artificial Sequences
<220> FEATURE:
<223> OTHER INFORMATION: Synthetic

<400> SEQUENCE: 29
ctgggttttg atctcctcga tg                                      22

```
<210> SEQ ID NO 30
<211> LENGTH: 23
<212> TYPE: DNA
<213> ORGANISM: Artificial Sequences
<220> FEATURE:
<223> OTHER INFORMATION: Synthetic

<400> SEQUENCE: 30
tcaccattgt cgtctgtatg gca                                            23

<210> SEQ ID NO 31
<211> LENGTH: 23
<212> TYPE: DNA
<213> ORGANISM: Artificial Sequences
<220> FEATURE:
<223> OTHER INFORMATION: Synthetic

<400> SEQUENCE: 31
ccaggttggc tccatatgaa atg                                            23

<210> SEQ ID NO 32
<211> LENGTH: 65
<212> TYPE: DNA
<213> ORGANISM: Artificial Sequences
<220> FEATURE:
<223> OTHER INFORMATION: Synthetic
<220> FEATURE:
<221> NAME/KEY: misc_feature
<222> LOCATION: (26)..(31)
<223> OTHER INFORMATION: n is a, c, g, or t

<400> SEQUENCE: 32
caagcagaag acggcatacg agatannnnn ngtgactgga gttcagacgt gtgctcttcc    60
gatct                                                                65

<210> SEQ ID NO 33
<211> LENGTH: 62
<212> TYPE: DNA
<213> ORGANISM: Artificial Sequences
<220> FEATURE:
<223> OTHER INFORMATION: Synthetic

<400> SEQUENCE: 33
aatgatacgg cgaccaccga gatctacaca cactctttcc ctacacgacg ctcttccgat    60
ct                                                                   62
```

DETECTION METHODS BASED ON SEQUENCING

CROSS-REFERENCE TO RELATED APPLICATIONS

This application is a U.S. National Phase of International Patent Application No. PCT/CN2015/000784, filed Nov. 10, 2015, which claims priority to Chinese Patent Application No. 201410643497.9, filed on Nov. 10, 2014, published as CN 104372093 A on Feb. 25, 2015, and the content of each application is incorporated by reference herein in its entirety for all purposes.
Sequence Listing on ASCII Text
This patent or application file contains a Sequence Listing submitted in computer readable ASCII text format (file name: 4565-2008900_SeqList.txt; date recorded: Jul. 12, 2018; and size: 7,000 bytes). The content of the Sequence Listing file is incorporated herein by reference in its entirety.

TECHNICAL FIELD

The present disclosure relates to the field of biotechnology, in particular to an SNP or mutation detection method based on sequencing technology, such as high-throughput sequencing or second generating sequencing.

BACKGROUND

SNP has extremely important value in molecular diagnostics, clinical testing, pathogen detection, forensics, genetic disease research, development of individual therapy and drugs, and many other fields (Gayet-Ageron et al., 2009). SNP detection is one of the main contents of the current genetic diagnosis. At the same time, genetic diagnosis represented by SNP detection has become an important means of screening newborns or specific populations for genetic diseases. Therefore, an easy-to-operate, low-cost and high-throughput SNP detection method is key to genetic testing.

The second generation of high-throughput sequencing technology is more accurate, sensitive, with higher throughput compared to other high-throughput gene detection technology. It has been involved in various aspects of life science and medical research with its lower prices and expanding range of applications. The use of high-throughput sequencing technology for high-throughput SNP detection is one of the current research focuses.

Currently, second-generation sequencing technologies are needed to build sequencing library. The sequencing libraries are then used for sequencing. The general steps include DNA extraction, DNA fragmentation, fragment selection, library construction (including adding connectors, amplification and other steps). The last step of machine sequencing is the data analysis. Among these steps, library construction takes the most time and effort, and in the process of building a database, the sample genes are amplified multiple times and are therefore prone to bias. Building a database using this method, all the genome fragments have the same chance of being sequenced. Therefore, this method is suitable for genome sequencing. If only one of some genes or only a specific part of the sequence is to be detected, this method would be a waste of sequencing space and would increase the difficulty of data analysis. In addition, samples treated in this way need complicated steps, need a huge complex sequencing data, require high initial amount of nucleic acid, and it is difficult for large-scale sequencing of samples simultaneously.

For some of the specific gene (such as exons, some single-gene disease-causing gene), sequencing will require additional steps to building a database target sequence enrichment. Currently the most widely used method is to capture the enrichment of target sequences by hybridization. The widely used target sequence capture technology is mainly based on solid-phase hybridization (Choi et al. 2009) or liquid phase hybridization capture technology to capture (Bainbridge et al. 2010). An existing custom capture commercial kit can be used (e.g., NimbleGen sequence capture array or Aglient sureselect target enrichment system, etc.), but these commercial custom sequence capture kits are generally expensive, and once the chips are customized, the target sequences to be detected are fixed and cannot be changed. In addition to the use of the target sequence capture technology for gene sequencing studies, the PCR technique based on non-hybrid sequence capture technology has also been applied, but there's the disadvantage of multiplex PCR-based technologies. For example, some areas will not be effectively amplified. Meanwhile, due to the amplification of errors by polymerases, and that all of the genetic fragments are mixed and amplified, the sequencing results are difficult to verify.

Illumina offers a different PCR amplification method to build a database (TruSeq custom amplicon). Through the probe and target specific sequence hybridization, two probes are anchored to the target sequence at the 5' and 3' ends. DNA polymerase extends to fill the gap (e.g., the sequence of interest) between the two probes, followed by sequencing. This method requires design of different measured probes for the gene sequences. It is complex and the quality of the database will be greatly influenced by the hybridization efficiency. When using this method to detect low-frequency mutations, it would waste sequencing space, because the vast majority of sequences being sequenced are wild-type sequences. It needs to increase the depth of sequencing to achieve compliance with the requirements of sensitivity. Using this method for large-scale population mutated genetic screening, wild-type sequences will take up most of the sequencing space, resulting in increased cost of sequencing. In addition, using this method, each sample requiring up to several hundred ng amount of nucleic acid is not conducive to lower concentrations of some rare or difficult to obtain samples of nucleic acid sequencing.

In order to address the shortcomings of these approaches, there is a need for a high-throughput sequencing method to build libraries for SNP detection.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, disclosed herein is a probe set for analyzing a genetic locus of a target polynucleotide sequence, comprising: one or more first probes comprising: (1) a first hybridization sequence that specifically binds to the target polynucleotide sequence upstream of the genetic locus, and (2) a first primer sequence upstream of the first hybridization sequence, wherein the first primer sequence does not bind to the target polynucleotide sequence; and one or more second probes comprising: (i) a second hybridization sequence that specifically binds to the target polynucleotide sequence downstream of the genetic locus, and (ii) a second primer sequence downstream of the second hybridization sequence, wherein the second primer sequence does not bind to the target polynucleotide sequence, wherein: the extension directions of the first and second probes are the same; and the first and second probes, when coupled, form a sequence comprising the genetic locus.

In one embodiment, in a probe set herein, the genetic locus comprises an SNP or a point mutation; the first hybridization sequence of the one or more first probes specifically binds to the target polynucleotide sequence upstream of the SNP or point mutation, and the 3' terminal nucleotide of the one or more first probes is complementary to the nucleotide at the SNP or point mutation locus; and the second hybridization sequence of the one or more second probes specifically binds to the target polynucleotide sequence downstream of the SNP or point mutation, and the 5' terminal nucleotide of the one or more second probes is complementary to the nucleotide immediately downstream of the SNP or point mutant locus.

In another embodiment, in a probe set herein, the genetic locus comprises an insertion at the nth residue of a wild-type target polynucleotide sequence; the one or more first probes comprise at least two first probes, one of which specifically binds to the wild-type target polynucleotide sequence until and excluding the nth residue, while the other specifically binds to the target polynucleotide sequence including and until the last residue of the inserted sequence; and the second hybridization sequence of the one or more second probes specifically binds to the target polynucleotide sequence downstream of the insertion, and the 5' terminal nucleotide of the one or more second probes is complementary to nth residue.

In another embodiment, in a probe set herein, the genetic locus comprises a deletion at the nth residue of a wild-type target polynucleotide sequence; the one or more first probes comprise at least two first probes, one of which specifically binds to the wild-type target polynucleotide sequence until and excluding the nth residue, while the other specifically binds to the target polynucleotide sequence until the first residue immediately upstream of the deleted sequence; and the second hybridization sequence of the one or more second probes specifically binds to the target polynucleotide sequence downstream of the deletion, and the 5' terminal nucleotide of the one or more second probes is complementary to nth residue.

In one aspect, provided herein is a probe set for analyzing a genetic locus of a target polynucleotide sequence, comprising: one or more first probes comprising: (1) a first hybridization sequence that specifically binds to the target polynucleotide sequence upstream of or including the genetic locus, and (2) a first primer sequence upstream of the first hybridization sequence, wherein the first primer sequence does not bind to the target polynucleotide sequence; and one or more second probes comprising: (i) a second hybridization sequence that specifically binds to the target polynucleotide sequence downstream of or starting from the genetic locus, and (ii) a second primer sequence downstream of the second hybridization sequence, wherein the second primer sequence does not bind to the target polynucleotide sequence, wherein the extension directions of the first and second probes are the same; the first probe is upstream of the second probe; and the first and second probes are adjacent and, when coupled, form a sequence comprising the genetic locus.

In one embodiment, the genetic locus comprises an SNP or a point mutation; and the first hybridization sequence of the one or more first probes specifically binds to the target polynucleotide sequence including the SNP or point mutation, and the 3' terminal nucleotide of the one or more first probes is complementary to the nucleotide at the SNP or point mutation locus, and the second hybridization sequence of the one or more second probes specifically binds to the target polynucleotide sequence downstream of the SNP or point mutation, and the 5' terminal nucleotide of the one or more second probes is complementary to the nucleotide immediately downstream of the SNP or point mutant locus; or the first hybridization sequence of the one or more first probes specifically binds to the target polynucleotide sequence upstream of the SNP or point mutation, and the 3' terminal nucleotide of the one or more first probes is complementary to the nucleotide immediately upstream of the SNP or point mutation locus, and the second hybridization sequence of the one or more second probes specifically binds to the target polynucleotide sequence starting from the SNP or point mutation, and the 5' terminal nucleotide of the one or more second probes is complementary to the nucleotide at the SNP or point mutation locus.

In any of the preceding embodiments, the 5' terminus of the one or more second probes can be phosphorylated. In any of the preceding embodiments, the first primer sequence of the one or more first probes can be a universal primer sequence.

In any of the preceding embodiments, the first primer sequence of the one or more first probes can uniquely identify the residue at the SNP or mutant locus.

In any of the preceding embodiments, the second primer sequence of the one or more second probes can be a universal primer sequence.

In one aspect, the genetic locus comprises a deletion or insertion.

In any of the preceding embodiments, the genetic locus can comprise an insertion at the $n^{th}$ residue of a wild-type target polynucleotide sequence; and the one or more first probes can comprise at least two first probes, one of which specifically binds to the wild-type target polynucleotide sequence until and excluding the $n^{th}$ residue, while the other specifically binds to the target polynucleotide sequence including and until the last residue of the inserted sequence, and the second hybridization sequence of the one or more second probes specifically binds to the target polynucleotide sequence downstream of the insertion, and the 5' terminal nucleotide of the one or more second probes is complementary to $n^{th}$ residue; or the one or more second probes can comprise at least two second probes, one of which specifically binds to the wild-type target polynucleotide sequence starting from the $n^{th}$ residue, while the other specifically binds to the target polynucleotide sequence including and from the first residue of the inserted sequence, and the first hybridization sequence of the one or more first probes specifically binds to the target polynucleotide sequence upstream of the insertion, and the 3' terminal nucleotide of the one or more first probes is complementary to the residue immediately upstream of $n^{th}$ residue in the wild-type target polynucleotide.

In any of the preceding embodiments, the genetic locus can comprise a deletion at the $n^{th}$ residue of a wild-type target polynucleotide sequence; the one or more first probes can comprise at least two first probes, one of which specifically binds to the wild-type target polynucleotide sequence until and excluding the $n^{th}$ residue, while the other specifically binds to the target polynucleotide sequence until the first residue immediately upstream of the deleted sequence, and the second hybridization sequence of the one or more second probes specifically binds to the target polynucleotide sequence downstream of the deletion, and the 5' terminal nucleotide of the one or more second probes is complementary to n$^{th}$ residue; or the one or more second probes can comprise at least two second probes, one of which specifically binds to the wild-type target polynucleotide sequence starting from the n$^{th}$ residue, while the other specifically binds to the target polynucleotide sequence including and from the first residue of the deleted sequence, and the first hybridization sequence of the one or more first probes specifically binds to the target polynucleotide sequence upstream of the deletion, and the 5' terminal nucleotide of the one or more first probes is complementary to the residue immediately upstream of n$^{th}$ residue in the wild-type target polynucleotide.

In any of the preceding embodiments, the first primer sequence of the one or more first probes can be a universal primer sequence. In any of the preceding embodiments, the two first probes can comprise different first primer sequences. In any of the preceding embodiments, the 5' terminus of the one or more second probes can be phosphorylated. In any of the preceding embodiments, the second primer sequence of the one or more second probes can be a universal primer sequence.

In any of the preceding embodiments, the genetic locus can be in a deafness related gene such as GJB2, SLC26A4, or 12SrRNA, wherein the genetic locus optionally comprises 1494C>T, IVS7-2A>G, 235delC, 176DEL16, and/or 299delAT. In one aspect, the one or more first probes for 1494C>T comprises the polynucleotide sequence set forth in SEQ ID NO: 21, SEQ ID NO: 22, SEQ ID NO: 23, and/or SEQ ID NO: 24. In any of the preceding embodiments, the one or more second probes for 1494C>T can comprise the polynucleotide sequence set forth in SEQ ID NO: 25. In any of the preceding embodiments, the one or more first probes for IVS7-2A>G can comprise the polynucleotide sequence set forth in SEQ ID NO: 7, SEQ ID NO: 8, SEQ ID NO: 9, and/or SEQ ID NO: 10. In any of the preceding embodiments, the one or more second probes for IVS7-2A>G can comprise the polynucleotide sequence set forth in SEQ ID NO: 11. In any of the preceding embodiments, the one or more first probes for 235delC can comprise the polynucleotide sequence set forth in SEQ ID NO: 15 and/or SEQ ID NO:16. In any of the preceding embodiments, the one or more second probes for 235delC can comprise the polynucleotide sequence set forth in SEQ ID NO: 17. In any of the preceding embodiments, the one or more first probes for 176DEL16 can comprise the polynucleotide sequence set forth in SEQ ID NO: 12 and/or SEQ ID NO:13. In any of the preceding embodiments, the one or more second probes for 176DEL16 can comprise the polynucleotide sequence set forth in SEQ ID NO: 14. In any of the preceding embodiments, the one or more first probes for 299delAT can comprise the polynucleotide sequence set forth in SEQ ID NO: 18 and/or SEQ ID NO:19. In any of the preceding embodiments, the one or more second probes for 299delAT can comprise the polynucleotide sequence set forth in SEQ ID NO: 20.

In one other aspect, provided herein is a kit for analyzing a genetic locus, comprising the probe set of any of the preceding embodiments. In one aspect, the kit further comprises a primer pair for amplifying 176del16, 299delAT, and/or 235delC. In another aspect, the primer pair for amplifying 176del16, 299delAT, and/or 235delC comprises the polynucleotide sequences set forth in SEQ ID NO: 28 and SEQ ID NO:29. In any of the preceding embodiments, the kit can further comprise a primer pair for amplifying 1494C>T. In one aspect, the primer pair for amplifying 1494C>T comprises the polynucleotide sequences set forth in SEQ ID NO: 26 and SEQ ID NO: 27. In any of the preceding embodiments, the kit can further comprise a primer pair for amplifying IVS7-2A>G. In one aspect, the primer pair for amplifying IVS7-2A>G comprises the polynucleotide sequences set forth in SEQ ID NO: 30 and SEQ ID NO: 31. In any of the preceding embodiments, one or both of the primers of the primer pair can be labeled. In one aspect, the label comprises biotin.

In any of the preceding embodiments, the kit can further comprise a barcode specific primer and/or a common primer. In one aspect, the barcode specific primer comprises the polynucleotide sequences set forth in SEQ ID NO: 32, and the common primer comprises the polynucleotide sequences set forth in SEQ ID NO: 33.

Also disclosed herein is a composition for analyzing at least a first genetic locus and a second genetic locus, comprising a first probe set of any one of any of the preceding embodiments for the first genetic locus, and a second probe set of any of the preceding embodiments for the second genetic locus. In one aspect, the probes in the first probe set are in equal molar amount, and the probes in the second probe set are in equal molar amount.

In any of the preceding embodiments, the first genetic locus can comprise an SNP or point mutation, and the second genetic locus can comprise a deletion and/or insertion. In one embodiment, the SNP or point mutation comprises 1494C>T, and/or IVS7-2A>G, and the deletion and/or insertion comprise 235delC, 176DEL16, and/or 299delAT.

In any of the preceding embodiments, the first and second probe sets can comprise at least two of the following probe sets: (1) a probe comprising the polynucleotide sequences set forth in SEQ ID NO: 25, and one or more of a probe comprising the polynucleotide sequences set forth in SEQ ID NO: 21, SEQ ID NO: 22, SEQ ID NO: 23, or SEQ ID NO: 24; (2) a probe comprising the polynucleotide sequences set forth in SEQ ID NO: 11, and one or more of a probe comprising the polynucleotide sequences set forth in SEQ ID NO: 7, SEQ ID NO: 8, SEQ ID NO: 9, or SEQ ID NO: 10; (3) a probe comprising the polynucleotide sequences set forth in SEQ ID NO: 17, and one or more of a probe comprising the polynucleotide sequences set forth in SEQ ID NO: 15 or SEQ ID NO: 16; (4) a probe comprising the polynucleotide sequences set forth in SEQ ID NO: 14, and one or more of a probe comprising the polynucleotide sequences set forth in SEQ ID NO: 12 or SEQ ID NO: 13; and (5) a probe comprising the polynucleotide sequences set forth in SEQ ID NO: 20, and one or more of a probe comprising the polynucleotide sequences set forth in SEQ ID NO: 18 or SEQ ID NO: 19.

In one aspect, provided herein is a method for analyzing a sample comprising a target polynucleotide sequence comprising a genetic locus, comprising: (a) contacting the sample with a probe set, the probe set comprising: one or more first probes comprising: (1) a first hybridization sequence that specifically binds to the target polynucleotide sequence upstream of or including the genetic locus, and (2) a first primer sequence upstream of the first hybridization sequence, wherein the first primer sequence does not bind to the target polynucleotide sequence; and one or more second probes comprising: (i) a second hybridization sequence that specifically binds to the target polynucleotide sequence downstream of or starting from the genetic locus, and (ii) a second primer sequence downstream of the second hybridization sequence, wherein the second primer sequence does not bind to the target polynucleotide sequence, wherein the extension directions of the first and second probes are the same, and the first probe is upstream of the second probe; (b) coupling the first and second probes bound to the target polynucleotide sequence to form a sequence comprising the genetic locus; (c) determining the sequence comprising the genetic locus, thereby determining the sequence of the genetic locus. In one aspect, the genetic locus comprises an SNP or a point mutation; and the first hybridization sequence of the one or more first probes specifically binds to the target polynucleotide sequence including the SNP or point mutation, and the 3' terminal nucleotide of the one or more first probes is complementary to the nucleotide at the SNP or point mutation locus, and the second hybridization sequence of the one or more second probes specifically binds to the target polynucleotide sequence downstream of the SNP or point mutation, and the 5' terminal nucleotide of the one or more second probes is complementary to the nucleotide immediately downstream of the SNP or point mutant locus; or the first hybridization sequence of the one or more first probes specifically binds to the target polynucleotide sequence upstream of the SNP or point mutation, and the 3' terminal nucleotide of the one or more first probes is complementary to the nucleotide immediately upstream of the SNP or point mutation locus, and the second hybridization sequence of the one or more second probes specifically binds to the target polynucleotide sequence starting from the SNP or point mutation, and the 5' terminal nucleotide of the one or more second probes is complementary to the nucleotide at the SNP or point mutation locus. In any of the preceding embodiments, the 5' terminus of the one or more second probes can be phosphorylated. In any of the preceding embodiments, the first primer sequence of the one or more first probes can be a universal primer sequence. In any of the preceding embodiments, the first primer sequence of the one or more first probes can be unique for the residue at the SNP or mutant locus. In any of the preceding embodiments, the second primer sequence of the one or more second probes can be a universal primer sequence.

In one aspect of a method disclosed herein, the genetic locus comprises a deletion or insertion. In one aspect, the genetic locus comprises an insertion at the $n^{th}$ residue of a wild-type target polynucleotide sequence; and the one or more first probes comprise at least two first probes, one of which specifically binds to the wild-type target polynucleotide sequence until and excluding the $n^{th}$ residue, while the other specifically binds to the target polynucleotide sequence including and until the last residue of the inserted sequence, and the second hybridization sequence of the one or more second probes specifically binds to the target polynucleotide sequence downstream of the insertion, and the 5' terminal nucleotide of the one or more second probes is complementary to $n^{th}$ residue; or the one or more second probes comprise at least two second probes, one of which specifically binds to the wild-type target polynucleotide sequence starting from the $n^{th}$ residue, while the other specifically binds to the target polynucleotide sequence including and from the first residue of the inserted sequence, and the first hybridization sequence of the one or more first probes specifically binds to the target polynucleotide sequence upstream of the insertion, and the 3' terminal nucleotide of the one or more first probes is complementary to the residue immediately upstream of $n^{th}$ residue in the wild-type target polynucleotide. In another aspect, the genetic locus comprises a deletion at the $n^{th}$ residue of a wild-type target polynucleotide sequence; the one or more first probes comprise at least two first probes, one of which specifically binds to the wild-type target polynucleotide sequence until and excluding the $n^{th}$ residue, while the other specifically binds to the target polynucleotide sequence until the first residue immediately upstream of the deleted sequence, and the second hybridization sequence of the one or more second probes specifically binds to the target polynucleotide sequence downstream of the deletion, and the 5' terminal nucleotide of the one or more second probes is complementary to $n^{th}$ residue; or the one or more second probes comprise at least two second probes, one of which specifically binds to the wild-type target polynucleotide sequence starting from the $n^{th}$ residue, while the other specifically binds to the target polynucleotide sequence including and from the first residue of the deleted sequence, and the first hybridization sequence of the one or more first probes specifically binds to the target polynucleotide sequence upstream of the deletion, and the 5' terminal nucleotide of the one or more first probes is complementary to the residue immediately upstream of $n^{th}$ residue in the wild-type target polynucleotide.

In any of the preceding embodiments, the first primer sequence of the one or more first probes can be a universal primer sequence. In any of the preceding embodiments, the two first probes can comprise different first primer sequences. In any of the preceding embodiments, the 5' terminus of the one or more second probes can be phosphorylated. In any of the preceding embodiments, the second primer sequence of the one or more second probes can be a universal primer sequence. In any of the preceding embodiments, the genetic locus can be in a deafness related gene such as GJB2, SLC26A4, or 12SrRNA, wherein the genetic locus optionally comprises 1494C>T, IVS7-2A>G, 235delC, 176DEL16, and/or 299delAT.

In any of the preceding embodiments, the one or more first probes for 1494C>T can comprise the polynucleotide sequence set forth in SEQ ID NO: 21, SEQ ID NO: 22, SEQ ID NO: 23, and/or SEQ ID NO: 24. In any of the preceding embodiments, the one or more second probes for 1494C>T can comprise the polynucleotide sequence set forth in SEQ ID NO: 25. In any of the preceding embodiments, the one or more first probes for IVS7-2A>G can comprise the polynucleotide sequence set forth in SEQ ID NO: 7, SEQ ID NO: 8, SEQ ID NO: 9, and/or SEQ ID NO: 10. In any of the preceding embodiments, the one or more second probes for IVS7-2A>G can comprise the polynucleotide sequence set forth in SEQ ID NO: 11. In any of the preceding embodiments, the one or more first probes for 235delC can comprise the polynucleotide sequence set forth in SEQ ID NO: 15 and/or SEQ ID NO:16. In any of the preceding embodiments, the one or more second probes for 235delC can comprise the polynucleotide sequence set forth in SEQ ID NO: 17. In any of the preceding embodiments, the one or more first probes for 176DEL16 can comprise the polynucleotide sequence set forth in SEQ ID NO: 12 and/or SEQ ID NO:13. In any of the preceding embodiments, the one or more second probes for 176DEL16 can comprise the polynucleotide sequence set forth in SEQ ID NO: 14. In any of the preceding embodiments, the one or more first probes for 299delAT can comprise the polynucleotide sequence set forth in SEQ ID NO: 18 and/or SEQ ID NO:19. In any of the preceding embodiments, the one or more second probes for 299delAT can comprise the polynucleotide sequence set forth in SEQ ID NO: 20.

In any of the preceding embodiments, the method can further comprise pre-amplification of the target polynucleotide sequence before the contacting step. In any of the preceding embodiments, the pre-amplification can comprise using a primer pair for amplifying a deafness related gene such as GJB2, SLC26A4, or 12SrRNA. In any of the preceding embodiments, the genetic locus can comprise 1494C>T, IVS7-2A>G, 235delC, 176DEL16, and/or 299delAT.

In any of the preceding embodiments, the pre-amplification can comprise using the primer pair having the polynucleotide sequences set forth in SEQ ID NO: 28 and SEQ ID NO: 29 to amplify 176del16, 299delAT, and/or 235delC. In any of the preceding embodiments, the pre-amplification can comprise using the primer pair having the polynucleotide sequences set forth in SEQ ID NO: 26 and SEQ ID NO: 27 to amplify 1494C>T. In any of the preceding embodiments, the pre-amplification can comprise using the primer pair having the polynucleotide sequences set forth in SEQ ID NO: 30 and SEQ ID NO: 31 to amplify IVS7-2A>G. In any of the preceding embodiments, one or both of the primers of the primer pair can be labeled. In any of the preceding embodiments, the label can comprise biotin.

In any of the preceding embodiments, the coupling step can comprise ligating the first and second probes bound to the target polynucleotide sequence. In any of the preceding embodiments, the determining step can comprise amplification and/or sequencing of the coupled sequences, such as high-throughput sequencing. In any of the preceding embodiments, the amplification and/or sequencing can comprise using a barcode specific primer and/or a common primer. In any of the preceding embodiments, the barcode specific primer can comprise the polynucleotide sequences set forth in SEQ ID NO: 32, and the common primer can comprise the polynucleotide sequences set forth in SEQ ID NO: 33.

BRIEF DESCRIPTION OF THE DRAWINGS

FIG. 2A is the testing result of 1494 wild-type plasmid. FIG. 2B is the testing result of IVS7-2 wild-type plasmid. FIG. 2C is the testing result of 176 wild-type plasmid. FIG. 2D is the testing result of 235 wild type plasmid. FIG. 2E is the testing result of 299 wild type plasmid.

FIG. 3A is the testing result of position 1494 (C:T=1:1). FIG. 3B is the testing result of position IVS7-2 (A:G=1:1). FIG. 3C is the testing result of position 176 (WT:MT=3:1). FIG. 3D is the testing result of position 235 (WT:MT=3:1). FIG. 3E is the testing result of position 299 (WT:MT=3:1).

FIG. 4A is the testing result of 1494 mutant plasmid. FIG. 4B is the testing result of IVS7-2 mutant plasmid. FIG. 4C is the testing result of position 176 (WT:MT=2:1). FIG. 4D is the testing result of position 235 (WT:MT=2:1). FIG. 4E is the testing result of position 299 (WT:MT=2:1).

DETAILED DESCRIPTION

Figure 1:
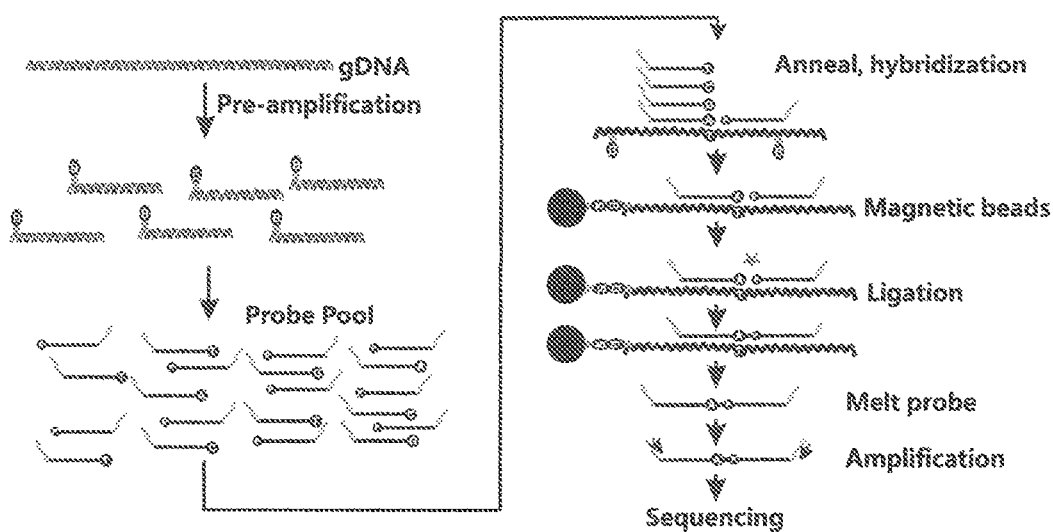
FIG. 1 is a schematic view of the detection method according to one aspect the present disclosure.

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications referred to in this application are incorporated by reference in their entireties for all purposes to the same extent as if each individual publication were individually incorporated by reference.

All headings are for the convenience of the reader and should not be used to limit the meaning of the text that follows the heading, unless so specified.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, polynucleotide synthesis and modification, polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer A Laboratory Manual* (2003); Bowtell and Sambrook, *DNA Microarrays: A Molecular Cloning Manual* (2003); Mount, *Bioinformatics: Sequence and Genome Anazvsis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Ausubel et al. eds., *Current Protocols in Molecular Biology* (1987); T. Brown ed., *Essential Molecular Biology* (1991), IRL Press; Goeddel ed., *Gene Expression Technology* (1991), Academic Press; A. Bothwell et al. eds., *Methods for Cloning and Analysis of Eukaryotic Genes* (1990), Bartlett Publ.; M. Kriegler, *Gene Transfer and Expression* (1990), Stockton Press; R. Wu et al. eds., *Recombinant DNA Methodology* (1989), Academic Press; M. McPherson et al., *PCR: A Practical Approach* (1991), IRL Press at Oxford University Press; Stryer, *Biochemistry* (4th Ed.) (1995), W. H. Freeman, New York N.Y.; Gait, *Oligonucleotide Synthesis: A Practical Approach* (2002), IRL Press, London; Nelson and Cox, *Lehninger, Principles of Biochemistry* (2000) 3rd Ed., W. H. Freeman Pub., New York, N.Y.; Berg, et al., *Biochemistry* (2002) 5th Ed., W. H. Freeman Pub., New York, N.Y., all of which are herein incorporated in their entireties by reference for all purposes.

As used herein, the singular forms "a", "an", and "the" include plural references unless indicated otherwise. For example, "a" sample includes one or more samples.

It is understood that aspects and embodiments of the disclosure described herein include "consisting" and/or "consisting essentially of" aspects and embodiments.

The term "binding" is used herein to refer to an attractive interaction between two molecules which results in a stable association in which the molecules are in close proximity to each other. Molecular binding can be classified into the following types: non-covalent, reversible covalent and irreversible covalent. Molecules that can participate in molecular binding include polypeptides, polynucleotides, carbohydrates, lipids, and small organic molecules such as pharmaceutical compounds. Polypeptides that form stable complexes with other molecules are often referred to as receptors while their binding partners are called ligands. Polynucleotides can also form stable complex with themselves or others, for example, DNA-protein complex, DNA-DNA complex, DNA-RNA complex.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acid ("PNA")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2', 5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

"Nucleic acid probe" and "probe" are used interchangeably and refer to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

As used herein, "complementary or matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s). The percentage of sequence identity or homology is calculated by comparing one to another when aligned to corresponding portions of the reference sequence.

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s). The percentage of sequence identity or homology is calculated by comparing one to another when aligned to corresponding portions of the reference sequence.

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa Nucleic Acids Res. 12:203 (1984).

The terms "homologous", "substantially homologous", and "substantial homology" as used herein denote a sequence of amino acids having at least 50%, 60%, 70%, 80% or 90% identity wherein one sequence is compared to a reference sequence of amino acids. The percentage of sequence identity or homology is calculated by comparing one to another when aligned to corresponding portions of the reference sequence.

In one aspect, provided herein is a method based on sequencing, such as high-throughput sequencing, to detect an SNP or mutation in a sample. In some embodiments, the mutation can include a point mutation, a deletion, an insertion, an indel, or a combination thereof.

In one embodiment, the method comprises designing one or more probes and/or one or more pre-amplification primer pairs, to detect one or more target sequences comprising the SNP(s) and/or mutation site(s). In any of the preceding embodiments, the mutation site(s) can be an SNP, a point mutation, an insertion, and/or a deletion.

In some embodiments, the one or more probes comprise one or more detection probes. In any of the preceding embodiments, the one or more detection probes can include one or more detection probes A for detecting the SNP(s) or point mutation(s). In any of the preceding embodiments, the one or more detection probes can further include one or more detection probes B for detecting the insertion(s) and/or deletion(s).

In any of the preceding embodiments, each of the detection probes A can correspond to and specifically detect an SNP or point mutation. For example, detection probes A for position IVS7-2 in the SLC26A1 gene and detection probes A for position 1494 of the 12SrRNA gene can be used in one or more reaction runs to detect the corresponding SNP or point mutation in a sample. The detection probes A for a specific SNP or point mutation position can comprise one or more probes ending in A, T, C, or G.

In any of the preceding embodiments, each of the detection probes B can correspond to and specifically detect an insertion or deletion.

In any of the preceding embodiments, the detection probes A for detecting one or more SNP sites can comprise one or more upstream genotyping probes ASO-A and one or more downstream site-specific probes LSO-A. In some embodiments, the ASO-A probe(s) and the LSO-A probe(s) have the same extending direction. In any of the preceding embodiments, the 3'end of an ASO-A probe can be identical or complementary to the target sequence of the SNP site (either wild-type or mutant). For example, two ASO-A probes can be used, one having a 3'end that is identical or complementary to the wild-type target sequence of the SNP site, and the other having a 3'end that is identical or complementary to the mutant target sequence of the SNP site.

In any of the preceding embodiments, the 3' terminal nucleotide of an ASO-A probe can be identical or complementary to the nucleotide at the wild-type or mutant SNP site. In any of the preceding embodiments, the 5' end of the ASO-A probe can be free from the target sequence of the SNP site. In another aspect, the 5' end of the ASO-A probe is separated from the target sequence. In some aspects, the ASO-A probe comprises a 5' end sequence that is not identical or complimentary to the target sequence, and the 5' end sequence does not hybridize to the target sequence or a complementary sequence thereof. In some aspects, the 5' end sequence comprises a common probe sequence P1.

In any of the preceding embodiments, each SNP or mutation can correspond to an ASO-A probe. For example, for a point mutation site where all four of A, T, C, or G is possible, four ASO-A probes can be designed for analyzing the site in a sample. Any one or more of the four ASO-A probes can be used in a reaction. Thus, the base at 3' end of the four ASO-A probes can be A, T, C, or G, respectively.

The 5' end of each of the ASO-A probes is free from the target sequence and comprises a universal probe P1.

In some embodiments, three of the four ASO-A probes can be used. For example, the bases at the 3' ends of two ASO-A probes are complementary to the SNP site in the wild-type or mutant status, respectively. The third ASO-A probe comprises a 3' terminal nucleotide that is different from the 3' terminal nucleotides of the first two ASO-A probes. The 5' end of each of the ASO-A probes is free from the target sequence and comprises a universal probe P1.

In some embodiments, two of the four ASO-A probes can be used. For example, the bases at the 3' ends of the two ASO-A probes are complementary to the SNP site in the wild-type or mutant status, respectively. The 5' end of each of the ASO-A probes is free from the target sequence and comprises a universal probe P1.

In some embodiments, one of the four ASO-A probes is used. The 3' terminal nucleotide of the ASO-B A probe is identical or complementary to the nucleotide at the SNP or mutation to be detected.

In any of the preceding embodiments, the 5' end of the LSO-A probe can be identical or complementary to the target sequence. In one aspect, the 5' terminal nucleotide of the LSO-A probe is identical or complementary to the first nucleotide of the target sequence immediately downstream of the SNP site in the direction of probe extension.

In any of the preceding embodiments, the 3'end of the LSO-A probe can be free from the target sequence of the SNP site. In another aspect, the 3' end of the LSO-A probe is separated from the target sequence. In some aspects, the LSO-A probe comprises a 3' end sequence that is not identical or complimentary to the target sequence, and the 3' end sequence does not hybridize to the target sequence or a complementary sequence thereof. In some aspects, the 3' end sequence comprises a common probe sequence P2.

In any of the preceding embodiments, the 5' end of the LSO-A probe can be phosphorylated. In one aspect, the 5' terminal nucleotide of the LSO-A probe is phosphorylated.

In any of the preceding embodiments, the detection probes B for detecting the insertion/deletion mutation site can comprise an upstream genotyping probe ASO-B for detecting the insertion/deletion mutation, an upstream genotyping probe ASO-B for detecting the wild-type sequence, and a downstream site-specific probe LSO-B. The three probes can have the same extending direction.

In one aspect, the upstream genotyping probe ASO-B for detecting the insertion/deletion mutation comprises an upstream genotyping probe ASO-B for detecting an insertion, and/or an upstream genotyping probe ASO-B for detecting a deletion.

In any of the preceding embodiments, the 3' end of the upstream genotyping probe ASO-B probe for detecting an insertion can comprise a sequence that is identical or complementary to the target sequence, and/or a sequence that is identical or complementary to the insertion sequence. In one aspect, the 3' terminal nucleotide of the ASO-B probe is identical or complementary to the last nucleotide of the inserted sequence, for example, the 5' terminal nucleotide of the inserted sequence.

The 3' end of the upstream genotyping probe ASO-B probe for detecting the wild-type sequence can be identical or complementary to the wild-type target sequence without the insertion, and in one aspect, the 3' terminal nucleotide of the ASO-B probe is identical or complementary to the nucleotide in the wild-type sequence immediately upstream of the insertion site.

In any of the preceding embodiments, the 3' end of the upstream genotyping probe ASO-B probe for detecting a deletion can comprise a sequence that is identical or complementary to the target sequence upstream of the deleted sequence, and/or a sequence that is identical or complementary to the target sequence downstream of the deleted sequence. In one aspect, the 3' terminal nucleotide of the ASO-B probe is identical or complementary to the nucleotide in the wild-type sequence that is immediately 5' to the first nucleotide of the deleted sequence. In one aspect, the 3' terminal nucleotide of the ASO-B probe is identical or complementary to the nucleotide in the wild-type sequence that is immediately upstream of the first nucleotide (in the 5' to 3' direction) of the deleted sequence. In one aspect, the 3' terminal nucleotide of the ASO-B probe is identical or complementary to the first upstream nucleotide next to the deletion site.

In some aspects, the target sequence of the insertion/deletion mutation site is the wild-type target sequence with insertion or deletion before the $n^{th}$ base.

In any of the preceding embodiments, the 5' end of the downstream site-specific probe LSO-B can be identical or complementary to the target sequence of the wild-type site, and the 5' end nucleotide can be identical or complementary to the $n^{th}$ nucleotide of the wild-type site sequence in the probe extending direction.

In any of the preceding embodiments, the 3' end of the LSO-B probe can be free from the target sequence and comprise a universal probe P2.

In any of the preceding embodiments, each upstream genotyping probe ASO and the corresponding downstream site-specific probe LSO of an SNP or mutation site can be coupled together without overlap or gap to obtain a sequence comprising the genetic locus to be analyzed. In one aspect, the sequence comprises a reverse complement sequence of the target sequence.

In any of the preceding embodiments, the coupling of the first and second probes can be performed by ligation. In other embodiments, the coupling can be performed by using one or more adaptors (such as an adaptor sequence that hybridizes to the target sequence in between the first and second probes), and then ligating the first probe to the adaptor and the adaptor to the second probe.

In any of the preceding embodiments, the pre-amplification primer pair can comprise one or more pre-amplification primer pairs. In one aspect, the pre-amplification primer pairs are capable of amplifying target sequences comprising one or more target SNP or mutation sites.

In any of the preceding embodiments, the 5' end of one primer in each of the pre-amplification primer pairs can be labeled, for example, with biotin.

In any of the preceding embodiments, the method disclosed herein can further comprise a step of pre-amplifying the test sample(s) using one or more of the pre-amplification primer pairs disclosed herein, for example, to obtain biotin-labeled polynucleotides of the target sequences.

In any of the preceding embodiments, the method disclosed herein can further comprise a step of using one or more of the detection probes A, a mixture of the detection probes A, one or more of the detection probes B, and/or a mixture of the detection probes B, to hybridize with the pre-amplified polynucleotides of the target sequences (such as the biotin-labeled nucleic acids) and obtain hybridization products.

In any of the preceding embodiments, the method disclosed herein can further comprise a step of ligating the hybridization products using a DNA ligase, to obtain one or more sequencing target sequences.

In any of the preceding embodiments, the method disclosed herein can further comprise a step of amplifying and sequencing the target sequence using a barcode specific primer and a common primer to obtain sequencing result of the target amplification products. In one aspect, the 20 bases of the 3' end of the barcode primer and the common primer are complementary to the universal probe sequence P1 or P2, respectively. In another aspect, the barcode specific primer comprises a barcode sequence XXXXXX, which is a random hexamer sequence of A, T, C, and G, and each combination can be used to identify a different sample.

In any of the preceding embodiments, the method disclosed herein can further comprise a step of analyzing the sequencing results to determine whether the test sample contains the mutation site and/or to determine the genotype(s) of the mutation site(s).

The analysis of the sequencing results to determine whether the test sample containing the mutation site or to determine the mutation site genotype can comprise comparing the reverse complementary sequence of a target sequence comprising a mutation with the sequencing results. The number of the sequences in the sequencing results having the same sequence as the reverse complementary sequence of the target sequence is recorded as the copy number of the mutation. The ratio of the mutation copy number in the total number of sequencing results is calculated. The genotype information of the site in the sample can then be determined based on the ratio.

In one aspect, analyzing the genotype information of the site is based on known information and statistical analysis, by setting an appropriate threshold, and determining the locus information according to the threshold.

In one embodiment, if the mutation site ratio is greater than 90%, the test sample contains or likely contains the mutation site, or the genotype of test sample is homozygous of the mutation site or a candidate of homozygous mutation site. If the mutation site ratio is 20-90%, the test sample contains or likely contains the mutation site, or the genotype of test sample is a heterozygous mutation site or a candidate of heterozygous mutation site. If the mutation site ratio is less than 20%, the test sample does not contain or likely does not contain the mutation site, or the genotype of test sample is wild-type or a candidate for wild-type sample.

The analysis of the sequencing results can comprise comparing the reverse complementary sequence of a wild-type target sequence with the sequencing results. The number of the sequences in the sequencing results having the same sequence as the reverse complementary sequence of the wild-type target sequence is recorded as the copy number of the wild-type sequences. The ratio of the wild-type copy number in the total number of sequencing results is calculated. The genotype information of the site in the sample can then be determined based on the ratio. The total number of sequencing results is equal to the total of the wild-type copy number and the mutant copy number.

In any of the preceding embodiments, the mutation site can be a SNP site and/or insertion/deletion mutation site.

In any of the preceding embodiments, the detection probe can comprise a plurality of detection probes A (for SNP or point mutation loci) and/or a plurality of detection probes B (for deletion and/or insertion).

In any of the preceding embodiments, each probe can be mixed in equimolar ratio.

In any of the preceding embodiments, the pre-amplification primers can comprise an equimolar mixture of the plurality of pre-amplification primer pairs.

In any of the preceding embodiments, the sample can be one or more samples, and each barcode specific primer can correspond to one sample.

In any of the preceding embodiments, the detection probes A can be a mixture of a plurality of the detection probes A in equimolar ratio.

In any of the preceding embodiments, the detection probes B can be a mixture of a plurality of the detection probes B in equimolar ratio.

In any of the preceding embodiments, after pre-amplification, the method can further comprise adding exonuclease I and/or alkaline phosphatase to the pre-amplification product to remove a pre-amplification primer and dNTP in the system, for example, to obtain the biotin-labeled nucleic acids.

In any of the preceding embodiments, the method can further comprise using magnetic beads to adsorb and capture the hybridization products.

In any of the preceding embodiments, the sequencing step can comprise using a second-generation sequencing method.

In any of the preceding embodiments, the detection probes can comprise two detection probes A for detecting an SNP or mutation, and three detection probes B for detecting a deletion and/or insertion.

In any of the preceding embodiments, the SNP sites can be 1494C>T and/or IVS7-2A>G.

In any of the preceding embodiments, the deletion or insertion mutation site can be 235delC, 176DEL16, and/or 299delAT.

In any of the preceding embodiments, detection probes A can comprise probes for 1494C>T. In one aspect, the probes can comprise an ASO-A probe comprising the polynucleotide sequence shown in SEQ ID NO: 21, an ASO-A probe comprising the polynucleotide sequence shown in SEQ ID NO: 22, an ASO-A probe comprising the polynucleotide sequence shown in SEQ ID NO: 23, and/or an ASO-A probe comprising the polynucleotide sequence shown in SEQ ID NO: 24. In any of the preceding embodiments, the probes can comprise a LSO-A probe, for example, a probe comprising the polynucleotide sequence shown in SEQ ID NO: 25.

In any of the preceding embodiments, detection probes A can comprise probes for IVS7-2A>G. In one aspect, the probes can comprise an ASO-A probe comprising the polynucleotide sequence shown in SEQ ID NO: 7, an ASO-A probe comprising the polynucleotide sequence shown in SEQ ID NO: 8, an ASO-A probe comprising the polynucleotide sequence shown in SEQ ID NO: 9, and/or an ASO-A probe comprising the polynucleotide sequence shown in SEQ ID NO: 10. In any of the preceding embodiments, the probes can comprise a LSO-A probe, for example, a probe comprising the polynucleotide sequence shown in SEQ ID NO: 11.

In any of the preceding embodiments, detection probes B can comprise probes for 235delC. In one aspect, the probes can comprise an ASO-B probe comprising the polynucleotide sequence shown in SEQ ID NO: 15, and/or an ASO-B probe comprising the polynucleotide sequence shown in SEQ ID NO: 16. In any of the preceding embodiments, the probes can comprise a LSO-B probe, for example, a probe comprising the polynucleotide sequence shown in SEQ ID NO: 17.

In any of the preceding embodiments, detection probes B can comprise probes for 176DEL16. In one aspect, the probes can comprise an ASO-B probe comprising the polynucleotide sequence shown in SEQ ID NO: 12, and/or an ASO-B probe comprising the polynucleotide sequence shown in SEQ ID NO: 13. In any of the preceding embodiments, the probes can comprise a LSO-B probe, for example, a probe comprising the polynucleotide sequence shown in SEQ ID NO: 14.

In any of the preceding embodiments, detection probes B can comprise probes for 299delAT. In one aspect, the probes can comprise an ASO-B probe comprising the polynucleotide sequence shown in SEQ ID NO: 18, and/or an ASO-B probe comprising the polynucleotide sequence shown in SEQ ID NO: 19. In any of the preceding embodiments, the probes can comprise a LSO-B probe, for example, a probe comprising the polynucleotide sequence shown in SEQ ID NO: 20.

In any of the preceding embodiments, the pre-amplification primers can comprise a primer pair for amplifying 176del16, 299delAT, and/or 235delC.

In any of the preceding embodiments, the pre-amplification primers can comprise a primer pair for amplifying 1494C>T.

In any of the preceding embodiments, the pre-amplification primers can comprise a primer pair for amplifying IVS7-2A>G.

In any of the preceding embodiments, the pre-amplification primers can comprise a primer pair having one primer comprising the single strand polynucleotide sequence of SEQ ID NO: 28 and another primer comprising the single strand polynucleotide sequence of SEQ ID NO: 29.

In any of the preceding embodiments, the pre-amplification primers can comprise a primer pair having one primer comprising the single strand polynucleotide sequence of SEQ ID NO: 26 and another primer comprising the single strand polynucleotide sequence of SEQ ID NO: 27.

In any of the preceding embodiments, the pre-amplification primers can comprise a primer pair having one primer comprising the single strand polynucleotide sequence of SEQ ID NO: 30 and another primer comprising the single strand polynucleotide sequence of SEQ ID NO: 31.

In one aspect, disclosed herein is a kit for detecting one or more SNPs or mutation sites. In one embodiment, the kit comprises one or more detection probes A for detecting 1494C>T, one or more detection probes A for detecting IVS7-2A>G, one or more detection probes B for detecting 235delC, one or more detection probes B for detecting 176DEL16, and/or one or more detection probes B for detecting 299delAT. In any of the preceding embodiments, the kit can further comprise a pre-amplification primer pair for amplifying 176del16, 299delAT, and/or 235delC, a pre-amplification primer pair for amplifying 1494C>T, a pre-amplification primer pair for amplifying IVS7-2A>G.

In any of the preceding embodiments, the mutation sites can comprise 1494C>T, IVS7-2A>G, 235delC, 176DEL16, and/or 299delAT.

In any of the preceding embodiments, the barcode primer nucleotide sequence can comprise the polynucleotide sequence of SEQ ID NO: 32.

In any of the preceding embodiments, the common primer nucleotide sequence can comprise the polynucleotide sequence of SEQ ID NO: 33.

In any of the preceding embodiments, detecting a plurality of SNPs and/or mutations can performed using a method disclosed herein. For example, a plurality of pre-amplification primers can be mixed to amplify different target polynucleotides in a sample. In another aspect, a plurality of detection probes can be mixed and hybridized to different target polynucleotides in the sample.

In any of the preceding embodiments, the mutation sites can comprise 235delC (deletion of C), 176del16 (deletion of 16 bp), 299delAT (deletion of AT), IVS7-2A>G (A mutated to G), and/or 1494C>T (C mutated to T).

In any of the preceding embodiments, the method can further comprise hybridization and capture of hybridization products by beads. In one aspect, appropriate concentrations of the detection probes ASO and LSO and a sample (with to without pre-treatment) are added to the reaction system. In another aspect, hybridization solution or binding buffer with appropriate salt concentrations are added. Then the reaction is subject to denaturation under high temperature, and then annealing under low-temperature, so that the ASO and LSO probe sequences and the sequences in the target polynucleotides around the SNP or mutation site are allowed to fully hybridize. After annealing is completed, beads are added, and the reaction is subjected to incubation under a suitable temperature. After completion of the incubation, a washing buffer and Taq ligation buffer are used to wash the beads to remove unhybridized probes.

After the washing is complete, a DNA ligase is used to ligate the probes bound to the target sequences at a suitable temperature. In one aspect, after coupling of the probes after ligation is completed, the ligation solution is discarded, and the beads are re-suspended in a suitable amount of ddH2O. Then, the re-suspended beads are heated to dissociate the ligated probes.

In one aspect, the ligated probes are amplified and/or sequenced using the barcode primer and/or the common primer to amplify, for example, by PCR.

In one aspect, the sample can be divided into two portions for hybridization. For one of the portions, only detection probes for the wild-type sequence are added for hybridization. For the other portion, detection probes for the mutant sequence (for example, for an SNP or point mutation, the other three probes except the wild-type probe) are added for hybridization. The samples are then subjected to ligation and amplified using the barcode primer and/or the common primer. The amplification products can be quantified, and the portions can be mixed according to a known ratio, which mixture is then subjected to sequencing, for example, high-throughput sequencing. This way, when such large-scale SNP mutation screening is used for detection of low frequency mutations, mutation-specific probes can be used only to detect mutant loci, thereby effectively using sequencing space and saving the cost of sequencing.

In some aspects, the technical improvements provided by a method herein include the following:

(1) The introduction of the pre-amplification step greatly increases the sensitivity of the system, such that nucleic acids lower than 50 copies could be detected.

(2) The sample labeling step is simple. The sample can be labeled during the progress of pre-amplification, without requiring additional labeling step.

(3) After pre-amplification, specific probes for detecting are used and enriched. Compared to the amplicon sequencing method, the present method excludes the impact of non-specific amplification product in pre-amplification. This is helpful for data analysis.

(4) The method of building a database is simple. Genomic fragments and artificial joints and other tedious steps are not required.

(5) Using a DNA ligase directly distinguishes SNP nucleotide and avoids the process of random mutation caused by extension, thereby improving the accuracy of sequencing.

(6) The probes can be used for large-scale sample screening, greatly reducing the cost of sequencing.

(7) Since all sequences are known, data analysis is easy.

(8) Site selection is flexible. The method is ideal for a moderate number of mutations for large-scale sample screening.

In one aspect, based on the feature of DNA ligases, the present disclosure provides a method of library construction, designing two adjacent probes according to the SNP site information. In one aspect, the 3' end of one of the probes corresponds to the SNP site. In one aspect, when two adjacent probes are completely complementary to the SNP site sequence, they can be ligated by a DNA ligase; otherwise it will not be ligated. By using the universal primer sequences in the probes, PCR amplification and library construction can be conducted. Then a second-generation sequencing technology can be used for high-throughput sequencing and analysis of the SNP site sequence information. In one aspect, simultaneous analysis of multiple loci can be achieved through a combination of different probes to detect multiple sites. Using barcode primers, samples can be mixed and each sample is identified by a barcode primer. For example, samples can be mixed according to known ratios and then sequenced at the same time, achieving multi-site, multi-sample and high-throughput testing. When carrying out large-scale population screening for mutations in the gene, mutant probe may be used alone to detect with more efficient use of sequencing space and lower cost.

Various embodiments in the device of the present disclosure are described in a progressive manner. Differences between various embodiments are emphasized in their specifications, while their common structures can be referred from the description.

Embodiment 1: A method based on high-throughput sequencing to detect the mutation site in test sample, comprising:

1) design probes and pre-amplification primer pairs to detect target sequences of known mutation sites, Said mutation sites are the SNP sites and insertions/deletions; Said detection probes are one or more detection probes A for detecting the SNP loci and/or one or more detection probes B for detecting insertions or deletion; said each probe A or probe B is corresponding to one of the mutation sites; Said detection probes A for detecting SNP sites comprise upstream genotyping probes ASO-A and downstream site-specific probes LSO-A, and said ASO-A probes and said LSO-A probes have the same extending direction; 3' end of said ASO-A probe is identical or complementary to the target sequence of the SNP site in wild-type or mutant; 3' terminal nucleotide of said ASO-A probe is identical or complementary to the SNP site in wild-type or mutant; 5' end of said ASO-A probe is free from the target sequence of the SNP site in wild-type or mutant, and a universal probe P1; Each said SNP mutations is corresponding to an ASO-A probe; 5' end of said LSO-A probe is identical or complementary to the target sequence of the SNP site in wild-type or mutant; 5' terminal nucleotide of said LSO-A probe, with the terminal nucleotide phosphorylation, is identical or complementary to the first nucleotide of target sequence of SNP site in the direction of probe extension, 3' end of said LSO-A probe is free from the target sequence, and a universal probe P2; Said detection probes B for detecting insertion/deletion mutation sites comprise a upstream genotyping probe ASO-B for detecting insertion/deletion mutations, a upstream genotyping probe ASO-B for detecting wild-type, and a downstream site-specific probe LSO-B; said three probes have the same extending direction; Said upstream genotyping probe ASO-B for detecting insertion/deletion mutations is upstream genotyping probes ASO-B for detecting insertion or upstream genotyping probes ASO-B for detecting deletion. 3' end of said upstream genotyping probe ASO-B probe for detecting insertion is identical or complementary to the target sequence of insertion site in wild-type or mutant; 3' terminal nucleotide of said ASO-B probe is identical or complementary to the last nucleotide of the insertion site; 3' end of said upstream genotyping probe ASO-B probe for detecting deletion is identical or complementary to the target sequence of deletion site in wild-type or mutant; 3' terminal nucleotide of said ASO-B probe is identical or complementary to the first upstream nucleotide next to the deletion site; Target sequence of insertion/deletion mutation sites is the wild-type target sequence with insertion or deletion before the nth bases. 5' end of the downstream site-specific probe LSO-B is identical or complementary to the target sequence of the wild-type site, and 5' end nucleotide is identical or complementary to the nth nucleotide of the wild-type site sequence in probe extending direction; 3' end of said LSO-B probe is free from the target sequence, and a universal probe P2; Each upstream genotyping probe ASO and corresponding downstream site-specific probe LSO of a mutation site splice together without overlapping or gap, obtaining the reverse complement sequence of the target sequence; Said pre-amplification primer pairs are one or more pre-amplification primer pair, said pre-amplification primer pairs are capable of amplifying the one or more target mutation sites; and 5' end of each of said pre-amplification primer pair is labeled with biotin;

2) conduct pre-amplification of the test samples by one or more pre-primer pairs to obtain a biotin labeled nucleic acid;

3) using one of said detection probes A, a mixture of plurality of the detection probe A, one of said detection probes B and/or a mixture of a plurality of said detection probes B, hybridize with said biotin labeled nucleic acid, and obtain hybridization product;

4) ligate said hybridization product using a DNA ligase, to obtain the sequencing target sequence;

5) amplify and sequence the target sequence by Barcode specific primer and Common primer to obtain sequencing result of the target amplification product; the 20 bases of 3' end of barcode primer and common primer is complementary to universal probe P1 or P2; said Barcode specific primers containing Barcode sequence XXXXXX sample which is a random sequence of A, T, C and G, determining different samples based on different combinations;

6) analyzing the sequencing results to determine whether the test sample containing the mutation site or to determine the genotype of the mutation site.

Embodiment 2: A method according to Embodiment 1, comprising: in step 1), said detection probes are plurality of detection probes A for detecting the SNP and plurality of detection probes B for detecting deletion or insertion mutation sites; each probe are mixed in equimolar ratio; in step 2), said plurality of said pre-amplification primer equimolar mixture of plurality of said pre-amplification primer pairs; said test sample is one or more, each barcode specific primer is corresponding to one test sample; in Step 3), said mixture of plurality of detection probes A is plurality of the detection probes in equimolar ratio; said mixture of a plurality of the detection probe B is plurality of the detection probe B in equimolar ratio.

Embodiment 3: The method according to Embodiment 1 or 2, comprising: in step 2), after pre-amplification, further comprising: adding exonuclease I and alkaline phosphatase to said pre-amplification product to remove pre-amplification primer and dNTP in the system, obtaining biotin labeled nucleic acid.

Embodiment 4: The method according to any one of Embodiment s 1-3, comprising: In step 3), during hybridization, magnetic beads adsorb and capture the hybridization product.

Embodiment 5: The method according to any one of Embodiment s 1-4, comprising: In step 5), the sequencing using second-generation sequencing instruments.

Embodiment 6: The method according to any one of Embodiment s 1-5, further comprising: said detection probes are 2 detection probe A for detecting SNP and 3 detection probe B for detecting deletion or insertion; said SNP sites are 1494C>T and IVS7-2A>G; said deletion or insertion mutation site is 235delC, 176DEL16 and 299delAT; said detection probe A corresponding to 1494C>T comprising probe ASO-A shown in SEQ ID No. 21, probe ASO-A shown in SEQ ID No. 22, probe ASO-A shown in SEQ ID No. 23, probe ASO-A shown in SEQ ID No. 24, and probe LSO-A shown in SEQ ID No. 25; said detection probe A corresponding to IVS7-2A>G comprising probe ASO-A shown in SEQ ID No. 7, probe ASO-A shown in SEQ ID No. 8, probe ASO-A shown in SEQ ID No. 9, probe ASO-A shown in SEQ ID No. 10, and probe LSO-A shown in SEQ ID No. 11; said detection probe A corresponding to 235delC comprising ASO-B probe shown in SEQ ID No. 15, ASO-A probe shown in SEQ ID No. 16, and LSO-B probe shown in SEQ ID No. 17; said detection probe A corresponding to 176DEL16 comprising ASO-B probe shown in SEQ ID No. 12, ASO-A probe shown in SEQ ID No. 13, and LSO-B probe shown in SEQ ID No. 14; said detection probe A corresponding to 299delAT comprising ASO-B probe shown in SEQ ID No. 18, ASO-A probe shown in SEQ ID No. 19, and LSO-B probe shown in SEQ ID No. 20; Said pre-amplification primers comprising primer pairs 1 for amplifying 176del16, 299delAT and 235delC, primer pairs 2 for amplifying 1494C>T, and primer pairs 3 for amplifying IVS7-2A>G; Said primer pairs 1 comprising single strand DNA shown in SEQ ID No. 28 and single strand DNA shown in SEQ ID No. 29; Said primer pairs 2 comprising single strand DNA shown in SEQ ID No. 26 and single strand DNA shown in SEQ ID No. 27; Said primer pairs 3 comprising single strand DNA shown in SEQ ID No. 30 and single strand DNA shown in SEQ ID No. 31.

Embodiment 7: A kit for detecting mutation sites comprising detection probe A for detecting 1494C>T, detection probe A for detecting IVS7-2A>G, detection probe B for detecting 235delC, detection probe B for detecting 176DEL16, detection probe B for detecting 299delAT, pre-amplification primer pairs 1 for amplifying 176del16, 299delAT and 235delC, pre-amplification primer pairs 1 for amplifying 1494C>T, pre-amplification primer pairs 2 for amplifying, and pre-amplification primer pairs 3 for amplifying IVS7-2A>G in Embodiment 6; said mutation sites are 1494C>T, IVS7-2A>G, 235delC, 176DEL16 and 299delAT.

EXAMPLES

All the methods used in the following examples are common unless otherwise specified. All the materials and reagents used in the following examples are commercially available unless otherwise specified. The present disclosure is illustrated by but not limited to the following examples. The quantitative tests of the following examples of were performed as triplicate experiments, and the results were averaged. FIG. 1 is an example showing a detection method of the present disclosure.

Example 1

Detection of Five Deafness Mutation Sites (SNP) Based on High-Throughput Sequencing Technology in Mixed Plasmid Samples In this example, multiple deafness sites were detected and plasmids for detecting the deafness sites are constructed by CapitalBio Corporation. Sequences of the plasmids were confirmed by sequencing validation. The information of the plasmids is shown in Table 1, and the mutations include SNP, deletion, and/or insertion.

TABLE 1

Information of the plasmids for deafness sites.

| Plasmid | Site information corresponding to mutations |
|---|---|
| pGEMT-299WT | 235WT、176WT、299WT |
| pCMV-235delC | 235delC、176WT、299WT |
| pCMV-176del16 | 235WT、176del16、299WT |
| pCMV-299delAT | 235WT、176WT、299delAT |
| pGEMT-IVSA | IVS7-2WT |
| pCMV-IVSG | IVS7-2A > G |
| pGEMT-1555WT | 1494WT |
| pCMV-1494C > T | 1494C > T |

NOTE:
WT means wild type, del means deletion, and > means SNP mutation.

Construction of Plasmid pGEMT-299WT:

human genomic DNA was amplified using primers XPMS0299F/XPMS0299R to obtain gene fragment 299WT containing the 235, 176, 299 sites. The 299WT fragment was then cloned into the vector pGEMT-easy.

Point mutations at site 235, 176, or 299 of the fragment 299WT were introduced, to obtain 235delC (in which the 235 C in the GJB2 gene was deleted, Reference Sequence GenBank No.: KF638275.1, submitted Nov. 30, 2013), 176del16 (in which the 16 residues of sites 176-191 in the GJB2 gene were deleted, Reference Sequence GenBank No.: KF638275.1, submitted Nov. 30, 2013), 299delAT (in which the 299-300 AT residues in the GJB2 gene were deleted, Reference Sequence GenBank No.: KF638275.1, submitted Nov. 30, 2013). Then the fragments were cloned into plasmid PCMV to obtain plasmids pCMV-235delC, pCMV-176del16, and pCMV-299delAT.

Construction of Plasmid pGEMT-IVSA:

human genomic DNA was amplified using primers XPMS0919F/XPMS0919R to obtain gene fragment IVSA containing the IVS7-2 site (the IVS7-2 site of the SLC26A4 gene, Reference Sequence GenBank No.: NG_008489, submitted Jul. 25, 2013). The fragment was then cloned into the vector pGEMT-easy.

Point mutations at IVSA sites of the IVS7-2 fragment were introduced, to obtain the IVS7-2A>G fragment (in which the A>G mutation occurred at the IVS7-2 site of the SLC26A4 gene, Reference Sequence GenBank No.: NG_008489, submitted Jul. 25, 2013). Then the fragments were cloned into plasmid PCMV by Nae I to obtain plasmid pCMV-IVSG.

Construction of Plasmid pGEMT-1555WT:

human genomic DNA was amplified using primers XPMS1555F/XPMS1555FR to get the gene fragment 1494WT containing the 1494 site (the 1494 site of mitochondrial gene 12SrRNA, Reference Sequence GenBank No.: J01415.2, submitted Jul. 17, 2013). The fragment was then cloned into the vector pGEMT-easy.

Point mutation at the 1494 site was introduced into the sequence of fragment 1494WT, to obtain the 1494C>T fragment (in which the C>T mutation occurred at the 1494 site in mitochondrial 12SrRNA gene, Reference Sequence GenBank No.: J01415.2, submitted Jul. 17, 2013). Then the fragments were cloned into plasmid PCMV by Nae I to obtain plasmid pCMV-1494C>T.

TABLE 2

Primers used for plasmid construction.

| Primer | Sequences |
|---|---|
| XPMS0299F | CCAGACTCAGAGAAGTCTCCC (SEQ ID No. 1) |
| XPMS0299R | ATGCTAGCGACTGAGCCTTGA (SEQ ID No. 2) |
| XPMS0919F | CGTGTAGCAGCAGGAAGTAT (SEQ ID No. 3) |
| XPMS0919R | AAGAGGAACACCACACTCAC (SEQ ID No. 4) |
| XPMS1555F | TGGCTAAGGTTGTCTGGTAG (SEQ ID No. 5) |
| XPMS1555R | CCCTGATGAAGGCTACAAAG (SEQ ID No. 6) |

(I) Probe and Pre-Amplification Primer Design (1) Test Sample Preparation

After quantification of the plasmids in Table 1, the plasmids were mixed as follows:

Experimental Group I:

The pGEMT-299WT, pGEMT-IVSA, and pGEMT-1555WT plasmids were mixed at equal copy numbers, e.g., $5 \times 10^3$ copies. In other words, the copy number of each of the 235WT, 176WT, 299WT, IVS7-2WT, and 1494WT plasmids was $5 \times 10^3$. Therefore, the five plasmids were present in the mixture at equal concentrations. The mixed plasmids were then diluted to obtain six test samples in which the copy number of each plasmid was $5 \times 10^3$, $10^3$, $5 \times 10^2$, $10^2$, $5 \times 10^1$, and $10^1$, respectively.

Experimental Group II:

$5 \times 10^3$ copies of each of plasmids pGEMT-299WT, pGEMT-IVSA, pGEMT-1555WT, pCMV-235delC, pCMV-299delAT, pCMV-176del16, pCMV-1494C>T, and pCMV-IVSG were mixed. The mixed plasmids were then diluted to obtain six test samples in which the copy number of each plasmid was $5 \times 10^3$, $10^3$, $5 \times 10^2$, $10^2$, $5 \times 10^1$, and $10^1$, respectively.

In Experimental Group II, according to the site information, in the mixed plasmids, 50% of the SLC26A4 plasmids were the mutated pCMV-IVSG plasmids (because pGEMT-IVSA and pCMV-IVSG had equal copy numbers), with dilution gradients of $5 \times 10^3$, $10^3$, $5 \times 10^2$, $10^2$, $5 \times 10^1$, and $10^1$. 50% of the 12SrRNA plasmids were the mutated pCMV-1494C>T plasmids (because pGEMT-1555WT and pCMV-1494C>T had equal copy numbers), with dilution gradients of $5 \times 10^3$, $10^3$, $5 \times 10^2$, $10^2$, $5 \times 10^1$, and $10^1$. Because the pGEMT-299WT, pCMV-235delC, pCMV-299delAT, and pCMV-176del16 plasmids had equal copy numbers, each of these plasmids represented 25% of the GJB2 plasmids, with dilution gradients of each mutation at $10^4$, $2 \times 10^3$, $4 \times 10^2$, $2 \times 10^2$, and $4 \times 10^1$.

Experimental Group III:

$5 \times 10^3$ copies of each of plasmids pCMV-235delC, pCMV-299delAT, pCMV-176del16, pCMV-1494C>T, and pCMV-IVSG were mixed. The mixed plasmids were then diluted to obtain six test samples in which the copy number of each plasmid was $5 \times 10^3$, $10^3$, $5 \times 10^2$, $10^2$, $5 \times 10^1$, and $10^1$, respectively.

In Experimental Group III, according to the site information, in the mixed plasmids, 100% of the SLC26A4 plasmids were the mutated pCMV-IVSG plasmids, with dilution gradients of $5 \times 10^3$, $10^3$, $5 \times 10^2$, $10^2$, $5 \times 10^1$, and $10^1$. 100% of the 12SrRNA plasmids were the mutated pCMV-1494C>T plasmids, with dilution gradients of $5 \times 10^3$, $10^3$, $5 \times 10^2$, $10^2$, $5 \times 10^1$, and $10^1$. Because the pCMV-235delC, pCMV-299delAT, and pCMV-176del16 plasmids had equal copy numbers, each of these plasmids represented 33% of the GJB2 plasmids, with dilution gradients of each mutation at $7.5 \times 10^3$, $3 \times 10^3$, $1.5 \times 10^3$, $3 \times 10^2$, $1.5 \times 10^2$, and $3 \times 10^1$.

(2) Probe and Pre-Amplification Primer Design

1) Probe Design

Principle:

Detection probes can be designed according to 40 bp nucleotides flanking the mutation site, for example, an SNP or an insertion and/or deletion mutation. Detection Probes A are used for detecting SNP sites, and Detection Probes B are used for detecting insertion and/or deletion sites. Each detection probe is between about 13 bp and about 25 bp.

Detection Probes A for detecting SNP sites can include the upstream genotyping probe ASO-A and the downstream site-specific probe LSO-A, and ASO-A and LSO-A probes have the same extending direction.

In one aspect, the 3' end of the ASO-A probe is identical or complimentary to the target sequence in which the wild-type or mutant residue at the SNP site is present. The 3' terminal nucleotide of the ASO-A probe is identical or complimentary to the wild-type or mutant residue of the SNP site. In another aspect, the 5' end of the ASO-A probe is separated from the target sequence in which the wild-type or mutant residue at the SNP site is present. In some aspects, the ASO-A probe comprises a 5' end sequence that is not identical or complimentary to the target sequence, and the 5' end sequence does not hybridize to the target sequence or a complementary sequence thereof. In some aspects, the 5' end sequence comprises a common probe sequence P1.

An ASO-A probe can be provided to correspond to each wildtype or mutant residue of a SNP site. For example, an ASO-A probe can be provided to correspond to 1494C of the 12SrRNA gene, and another ASO-A probe can be provided to correspond to 1494T of the 12SrRNA gene.

The 5' end of the LSO-A probe is identical or complementary to the target sequence. The 5' terminal nucleotide of the LSO-A, with a terminal nucleotide phosphorylation, is identical or complementary to the first nucleotide, of the target sequence, downstream of the SNP site in the extending direction of the probe. In one aspect, the 3' end of the LSO-A probe is separated from the target sequence in which the SNP site is present. In some aspects, the LSO-A probe comprises a 3' end sequence that is not identical or complimentary to the target sequence, and the 3' end sequence does not hybridize to the target sequence or a complementary sequence thereof. In some aspects, the 3' end sequence of the LSO-A comprises a universal probe sequence P2, for example, the 22nd-42nd nucleotides from the 5' end of SEQ ID NO: 11.

Detection Probes B for detecting insertion/deletion mutation can include an upstream genotyping probe ASO-B(1) for detecting an insertion and/or deletion mutation, an upstream genotyping probe ASO-B(2) for detecting the wild-type sequence, and a downstream site-specific probe LSO-B. All three probes have the same extending direction.

The upstream genotyping probe ASO-B for detecting the insertion and/or deletion mutation can include the ASO-B probe for detecting an insertion, and the ASO-B probe for detecting a deletion.

In one aspect, the 3' end of the ASO-B probe for detecting an insertion is identical or complimentary to the target sequence in which the insertion sequence is present. The 3' terminal nucleotide of the ASO-B probe is identical or complimentary to the terminal nucleotide of the insertion sequence.

In one aspect, the 3' end of the ASO-B probe for detecting a deletion is identical or complimentary to the target sequence in which the deletion is present. The 3' terminal nucleotide of the ASO-B probe is identical or complimentary to the first nucleotide immediately upstream to the deletion site.

Target sequence of insertion/deletion mutation sites is the wild-type target sequence with an insertion and/or deletion before the $n^{th}$ base.

The 5' end of the downstream site-specific probe LSO-B is identical or complementary to the target sequence of the wild-type site. The 5' terminal nucleotide is identical or complementary to the $n^{th}$ nucleotide of the wild-type site sequence in the probe extending direction.

In one aspect, the 3' end of the LSO-B probe is separated from the target sequence. In some aspects, the LSO-B probe comprises a 3' end sequence that is not identical or complimentary to the target sequence, and the 3' end sequence does not hybridize to the target sequence or a complementary sequence thereof. In some aspects, the 3' end sequence of the LSO-B comprises a universal probe sequence P2.

In some aspects, each upstream genotyping probe ASO and the corresponding downstream site-specific probe LSO of a mutation site can be spliced together without any overlapping nucleotide(s) or gap. The spliced sequence can provide the reverse complement sequence of the target sequence, either wild-type or mutant.

For example, Detection Probes A can include four upstream genotyping probes (ASO) and one downstream site-specific probe (LSO), as shown in FIG. 1. The ASO and LSO probes have the same extension direction, and can be spliced together without any overlap or gap, to obtain the reverse complement sequence of the target sequence.

In FIG. 1, four ASO-A probes can be used to detect a SNP. The 3' terminal nucleotide of the four ASO-A probes are A, T, C, and G, respectively; the 5' end of the ASO-A probes separate from the target sequence and comprise a universal probe P1 (for example, the $1^{st}$-$20^{th}$ nucleotides of the 5' end of SEQ ID NO: 7).

In some examples, three of the four ASO-A probes may be used, and two of the ASO-A probes can comprise a 3' terminal nucleotide that corresponds to the wild-type residue and the mutant residue of the SNP, respectively. The 3' end of the other ASO-A probe is different from the wild-type and the mutant residue of the SNP. The 5' ends of the ASO-A probes are separate from the target sequence and can comprise the universal probe P1 (for example, the $1^{st}$-$20^{th}$ nucleotides of the 5' end of SEQ ID NO: 7).

Alternatively, two of the four ASO-A probes may be used, each comprising a 3' terminal nucleotide that corresponds to the wild-type residue and the mutant residue of the SNP, respectively. The 5' ends of the ASO-A probes are separate from the target sequence and can comprise the universal probe P1 (for example, the $1^{st}$-$20^{th}$ nucleotides of the 5' end of SEQ ID NO: 7).

When detecting one particular SNP (i.e., one residue at the SNP site), one of the four ASO-A probes can be used, and the 3' end base of the ASO-A probe is identical or complementary to the SNP residue to be detected. The 5' end of the ASO-A probe is separate from the target sequence and can comprise the universal probe P1 (for example, the $1^{st}$-$20^{th}$ nucleotides of the 5' end of SEQ ID NO: 7).

The 5' end of the LSO probe with a terminal nucleotide phosphorylation is complementary to the target sequence, and the 5' terminal base of the LSO probe is complementary to the next base of the target sequence downstream of the SNP site in the probe extending direction. The 3' end of the LSO probe is separate from the target sequence and can comprise the universal probe P2 (for example, the $22^{nd}$-$42^{nd}$ nucleotides from the 5' end of SEQ ID NO: 11).

Detection Probes B can include the upstream genotyping probe for detecting the mutant sequence (ASO), the upstream genotyping probe for detecting the wild-type sequence (ASO), and the downstream site-specific probe (LSO). The probes have the same extension direction. In one aspect, the upstream genotyping probe and the downstream site-specific probe for detecting the mutant sequence can be spliced together without overlap or gap, to obtain the reverse complement sequence of the target sequence. In another aspect, the upstream genotyping probe and the downstream site-specific probe for detecting the wild-type sequence can be spliced together without overlap or gap, to obtain the reverse complement sequence of the wild-type target sequence. The mutant target sequence, in one aspect, is the wild-type target sequence with an insertion or deletion before the $n^{th}$ base.

According to the above design principles, detection probes were designed for the about 40 bp flanking sequences of the five deafness associated mutation sites (235delC, 176del16, 299delAT, IVS7-2A>G, 1494C>T). In order to ensure the sensitivity and specificity of the probes, the hybridizing region of the probe and the template is 13 nt for the 1494 site in the 12SrRNA gene and with a mutation GcCCG to GgCCG.

TABLE 3

Probe sequences.

| Probes | Sequences | Probe Type (name / type / mutation type / mutation bases) |
|---|---|---|
| IVSUG17 | ACACGACGCTCTTCCGATCTAGTAGCAATTATCGTCT (SEQ ID No. 7) | IVSUG17/ASO/snp/T |
| IVSUC17 | ACACGACGCTCTTCCGATCTAGTAGCAATTATCGTCA (SEQ ID No. 8) | IVSUG17/ASO/snp/A |
| IVSUA17 | ACACGACGCTCTTCCGATCTAGTAGCAATTATCGTCG (SEQ ID No. 9) | IVSUG17/ASO/snp/G |

TABLE 3-continued

Probe sequences.

| Probes | Sequences | Probe Type (name / type / mutation type / mutation bases) |
|---|---|---|
| IVSUT17 | ACACGACGCTCTTCCGATCTAGTAGCAATTATCGTCC (SEQ ID No. 10) | IVSUG17/ASO/snp/C |
| IVSD3 | GAAATAAAACAAAAGATGTTAGATCGGAAGAGCACACGTCT (SEQ ID No. 11) | IVSUG17/LSO |
| 176WU-2 | ACACGACGCTCTTCCGATCTCCAGGCTGCAAGAACGTGTG (SEQ ID No. 12) | 176/ASO/wild-type(WT) |
| 176MU-2 | ACACGACGCTCTTCCGATCTTGCAACACCCTGCAGCCAG (SEQ ID No. 13) | 176/ASO/deletion(MT) |
| 176DP | CTACGATCACTACTTCCCCAGATCGGAAGAGCACACGTCT (SEQ ID No. 14) | 176/LSO |
| 235WU | ACACGACGCTCTTCCGATCTACATCCGGCTATGGGCC (SEQ ID No. 15) | 235/ASO/ wild-type (WT) |
| 235MU | ACACGACGCTCTTCCGATCTCACATCCGGCTATGGGC (SEQ ID No. 16) | 235/ASO/deletion(MT) |
| 235DP | CTGCAGCTGATCTTCGTGTCGATCGGAAGAGCACACGTCT (SEQ ID No. 17) | 235/LSO |
| 299WU | ACACGACGCTCTTCCGATCTTGGCCTACCGGAGACAT (SEQ ID No. 18) | 235/ASO/ wild-type (WT) |
| 299MU | ACACGACGCTCTTCCGATCTCGTGGCCTACCGGAGAC (SEQ ID No. 19) | 299/ASO/deletion(MT) |
| 299DP | GAGAAGAAGAGGAAGTTCATGATCGGAAGAGCACACGTCT (SEQ ID No. 20) | 299/LSO |
| 1494UG13 | ACACGACGCTCTTCCGATCTACCGgCCGTCACG (SEQ ID No. 21) | 1494/ASO/snp/G |
| 1494UC13 | ACACGACGCTCTTCCGATCTACCGgCCGTCACC (SEQ ID No. 22) | 1494/ASO/snp/C |
| 1494UA13 | ACACGACGCTCTTCCGATCTACCGgCCGTCACA (SEQ ID No. 23) | 1494/ASO/snp/A |
| 1494UT13 | ACACGACGCTCTTCCGATCTACCGgCCGTCACT (SEQ ID No. 24) | 1494/ASO/snp/T |
| 1494DP | CTCCTCAAGTATACTTCAAAGATCGGAAGAGCACACGTCT (SEQ ID No. 25) | 1494/L50 |

2) Pre-Amplification Primer Design

Design Principle: Based on the nucleotide sequences to be detected, primers are designed to amplify the target sequence containing the mutation site. The primers are then used for sample pre-amplification and biotin labeling.

Pre-amplification primers were designed according to the 5 deafness mutations (IVS7-2A>G, 176del16 (16 bp deletion at the 176 site), 299delAT, 235delC, and 1494C>T).

TABLE 4

Pre-amplification primers sequences.

| Primers | Sequences |
|---|---|
| 1555F1 | AGTGCTTAGTTGAACAGGGCC (SEQ ID No. 26) |
| 1555R1-B | Biotin-GGTTCGTCCAAGTGCACTTTC (SEQ ID No. 27) |
| GJB234F1 | AAAGGAGGTGTGGGGAGATGA (SEQ ID No. 28) |
| GJB234R1-B | Biotin-CTGGGTTTTGATCTCCTCGATG (SEQ ID No. 29) |
| IVS7-2F1-B | Biotin-tcaCCATTGTCGTCTGTATGCA (SEQ ID No. 30) |
| IVS7-2R1 | CCAGGTTGGCTCCATATGAAatg (SEQ ID No. 31) |

The amplification products of GJB234F1/GJB234R1-B contain sequences comprising 176del16, 299delAT, and/or 235delC. The amplification products of 1555F1/1555R1-B contain sequences comprising the 1494C>T site. The amplification products of IVS7-2F1-B/IVS7-2R1 contain sequences comprising the IVS7-2A>G site.

The equimolar mix of the above six primers is named Multi-p3.

(II) Pre-Amplification

Pre-amplification was conducted using the above-mentioned Multi-p3 of the six samples in each group of Experimental Groups 1-3.

The pre-amplification system volume was 10 μL, containing 1 μL DNA template, 1 μL 1×PCR buffer, 0.5 U DNA polymerase, 1 μL biotin labeled mixed primers Multi-p3 (50 nM each for primer), 200 μM dNTP, 4.5 mM $MgCl_2$, with water added to bring up the total volume to 10 μL.

PCR condition: first, 95 degrees (Celsius) denaturation for 5 min, then 95 degrees (Celsius) denaturation for 20 s, 60 degrees (Celsius) annealing for 4 min; 20 Cycles. Biotin label was added in the pre-amplification process. After pre-amplification, final concentration 1 U/μL Exonuclease I (ExoI) and final concentration 0.1 U/μL alkaline phosphatase (AP) were added to the amplified products to remove primers and dNTPs in the pre-amplification system. After 37 degrees (Celsius) reaction for 3 h, 6 biotin-labeled nucleic acid samples in Experimental Group 1, 6 biotin-labeled nucleic acid samples in Experimental Group 2, and 6 biotin-labeled nucleic acid samples in Experimental Group 3 were obtained.

(III) Hybridization

The 19 probes in Table 3 were mixed in equal molar ratio to get the detection probes set.

Each biotin-labeled nucleic acid sample obtained in (II) above was hybridized with the detection probes set (each probe 100 at fmol), then the hybridization products were captured and absorbed by magnetic beads.

For example, each of the biotin-labeled nucleic acid sample (8 µL) and the detection probes set 2 µl (concentration of each probe—50 pM) were added into 20 µL hybridization buffer (2×) (100 mM Tris-HCl, 500 mM NaCl, 1 mM EDTA, 0.2% tween80, pH=7.6). The mixture was then subjected to high temperature denaturation, followed by low temperature annealing (95 degrees (Celsius) for 5 min, then 45 degrees (Celsius) for 10 min annealing), so that the probe ASO and LSO fully hybridized with flank sequences of the detection sites. Magnetic beads were then added, followed by 45 degrees (Celsius) incubation for 2 h. 1× washing buffer (50 mM Tris-HCl, 100 mM NaCl, 0.5 mM EDTA, 0.1% tween80, pH=7.6) and Taq ligation buffer (NEB) were used to wash the magnetic beads to remove the non-hybridized probes, obtaining 6 hybridization products in Experimental Group 1, 6 hybridization products in Experimental Group 2, and 6 hybridization products in Experimental Group 3.

(IV) Ligation

DNA ligase was added to the 6 hybridization products in Experimental Group 1, the 6 hybridization products in Experimental Group 2, and the 6 hybridization products in Experimental Group 3, and ligation reactions were performed. After ligation of perfectly matched probes, the ligation reaction buffer was removed, and the beads were re-suspended by ddH$_2$O. Then the reaction was incubated at 95 degrees (Celsius) for 5 min to melt the hybridized probes and obtain 6 ligated sequences in Experimental Group 1, 6 ligated sequences in Experimental Group 2 and 6 ligated sequences in Experimental Group 3.

(V) Amplification and Sequencing

```
Barcode primer:
                                    (SEQ ID NO: 32)
CAAGCAGAAGACGGCATACGAGATAXXXXXXGTGACTGGAGT

TCAGACGTGTGCTCTTCCGATCT.
```

XXXXXX is the barcode sequence to differentiate the samples, and the 6 bases can be random combinations of A, T, C, and G, to distinguish each sample.

```
Common primer:
                                    (SEQ ID NO: 33)
AATGATACGGCGACCACCGAGATCTACACACACTCTTTCCCTAC

ACGACGCTCTTCCGATCT.
```

The 20 bases of the 3' end of the barcode primer and the common primer are complementary sequences to P1 and P2, respectively. Using the barcode primer and the common primer, the 6 ligated sequences in Experimental Group 1, the 6 ligated sequences in Experimental Group 2, and the 6 ligated sequences in Experimental Group 3 were amplified by PCR. The amplified products were then extracted and sequencing was performed using second generation high-throughput sequencing instruments.

(VI) Data Analysis

Sequence alignment was conducted between the sequencing results and the reverse complementary sequences of each mutant or wild-type target sequence. The number of sequencing results that matched the target sequence was counted and used to calculate the proportion of the mutants in each sample.

The proportion of the mutants is the ratio of the mutation sites to the total sites, and the total site is the total of the mutation sites and wild-type sites. The proportion of the mutation was used to judge genotype information of the sites, using statistical analysis and setting appropriate threshold, then judging genotype information of the locus by the threshold.

In this example, if the mutation site ratio is greater than 90%, the test sample contains or likely contains the mutation site, or the genotype of test sample is homozygous of the mutation site or a candidate of homozygous mutation site. If the mutation site ratio is 20-90%, the test sample contains or likely contains the mutation site, or the genotype of test sample is a heterozygous mutation site or a candidate of heterozygous mutation site. If the mutation site ratio is less than 20%, the test sample does not contain or likely does not contain the mutation site, or the genotype of test sample is wild-type or a candidate for wild-type sample.

Figure 2:
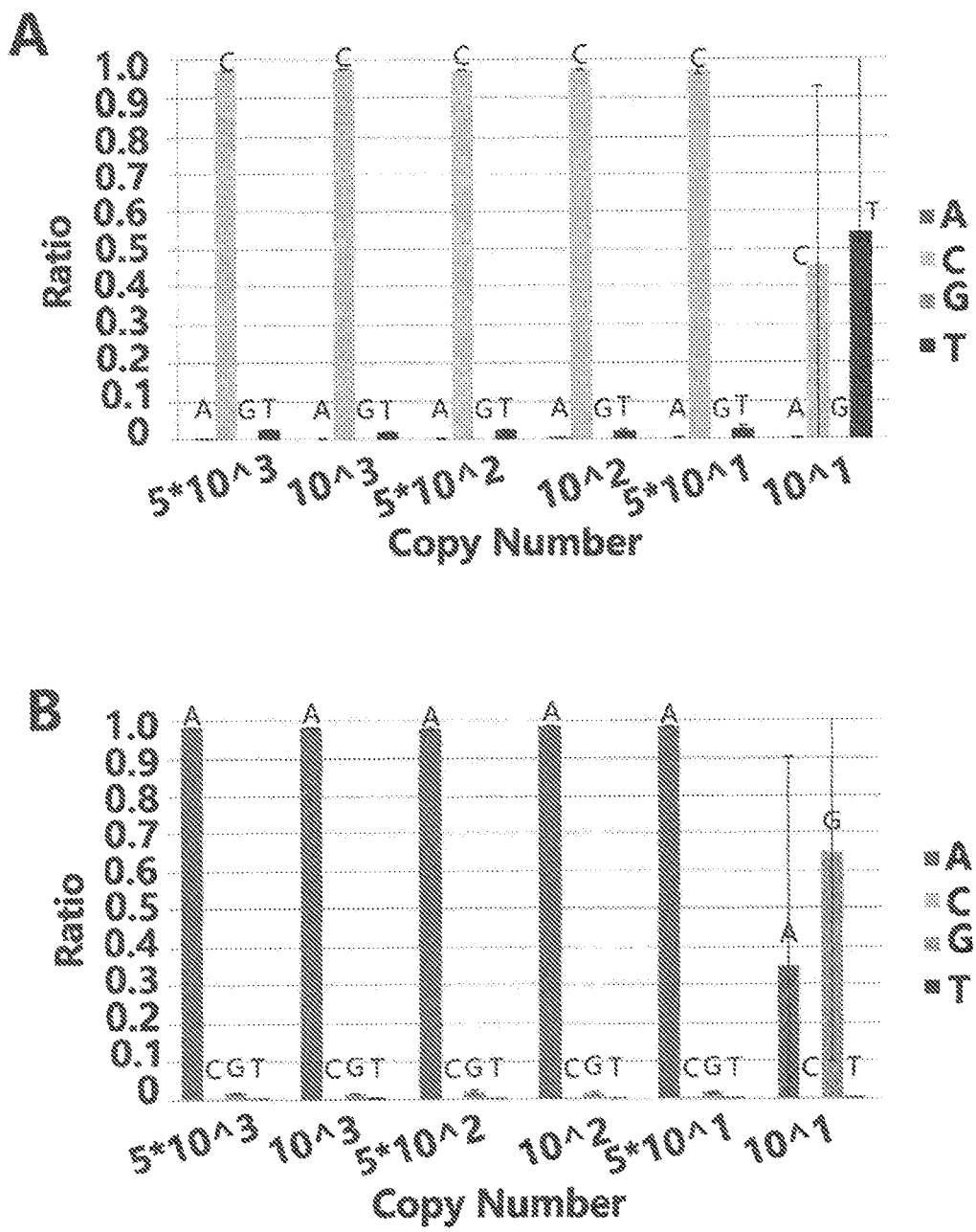
FIGS. 2A-2E are the testing results of plasmid group I.
Figure 2:
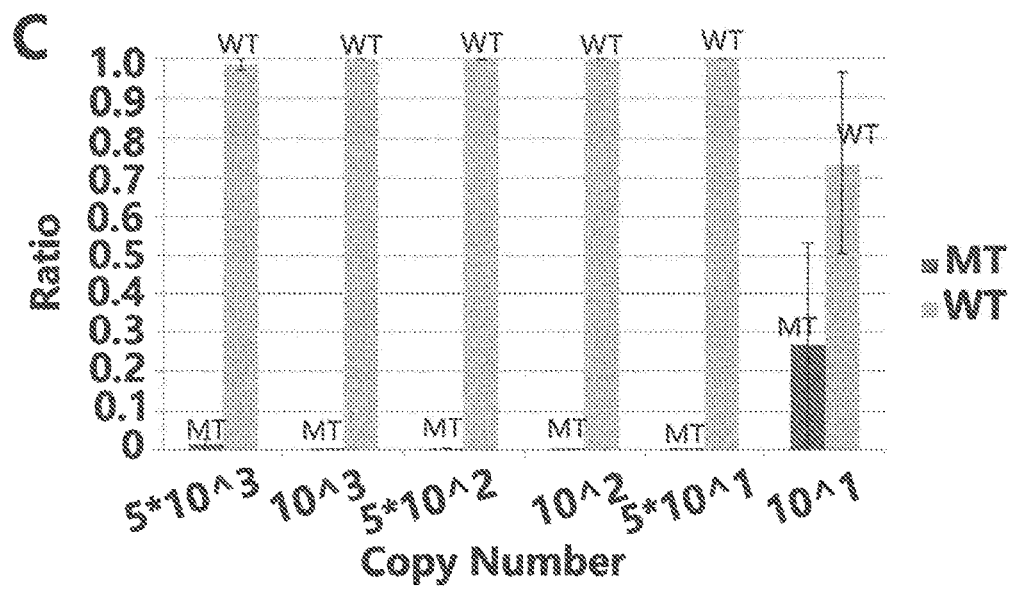
Figure 2:
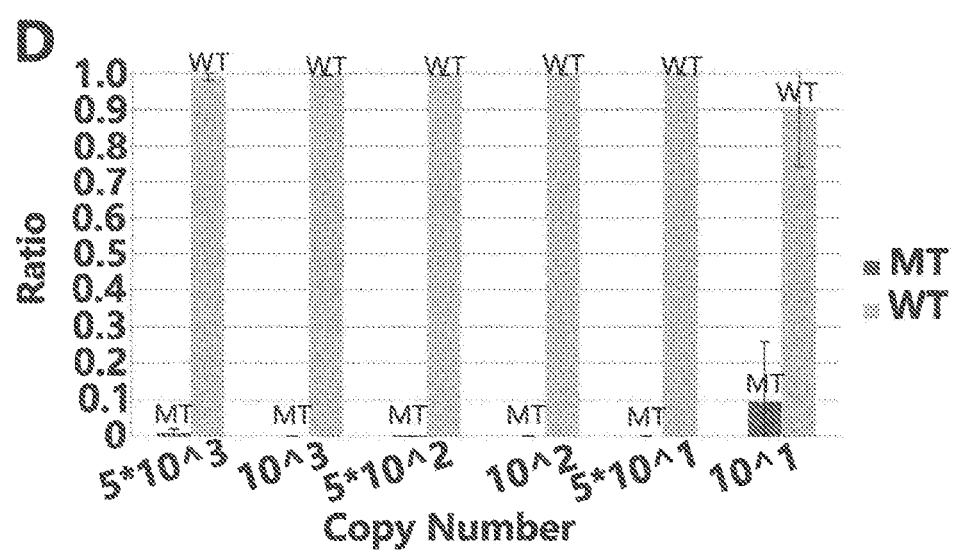
Figure 2:
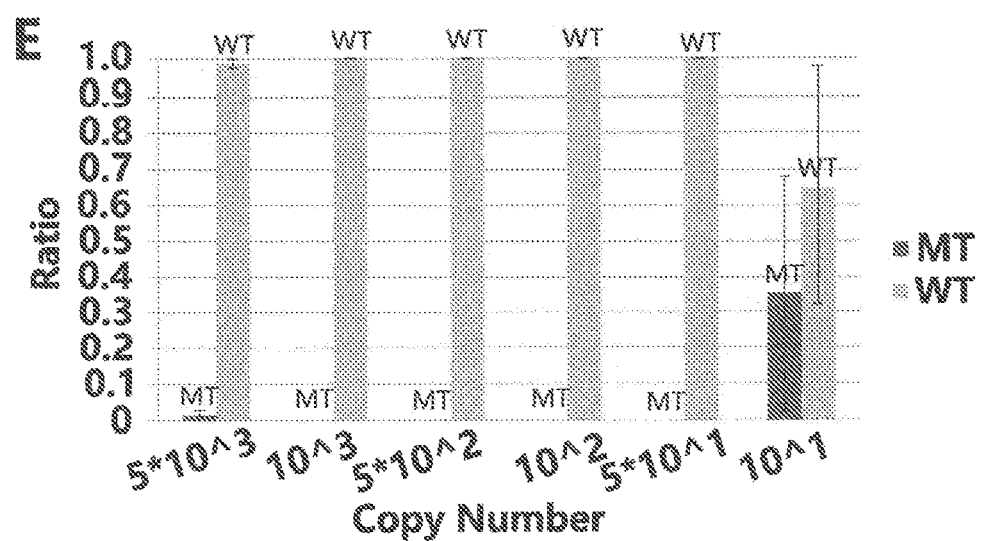
Figure 3:
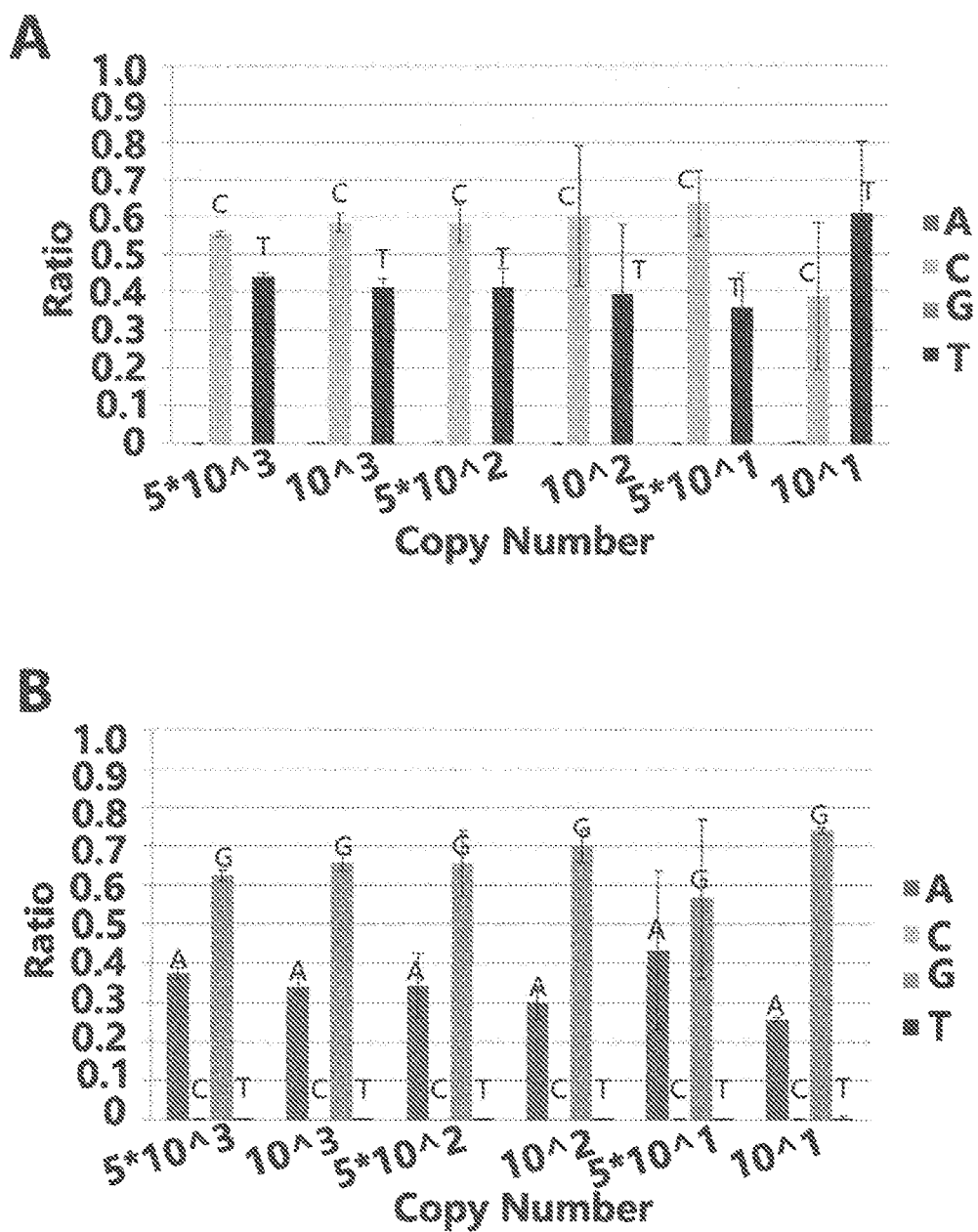
FIGS. 3A-3E are the testing results of plasmid group II.
Figure 3:
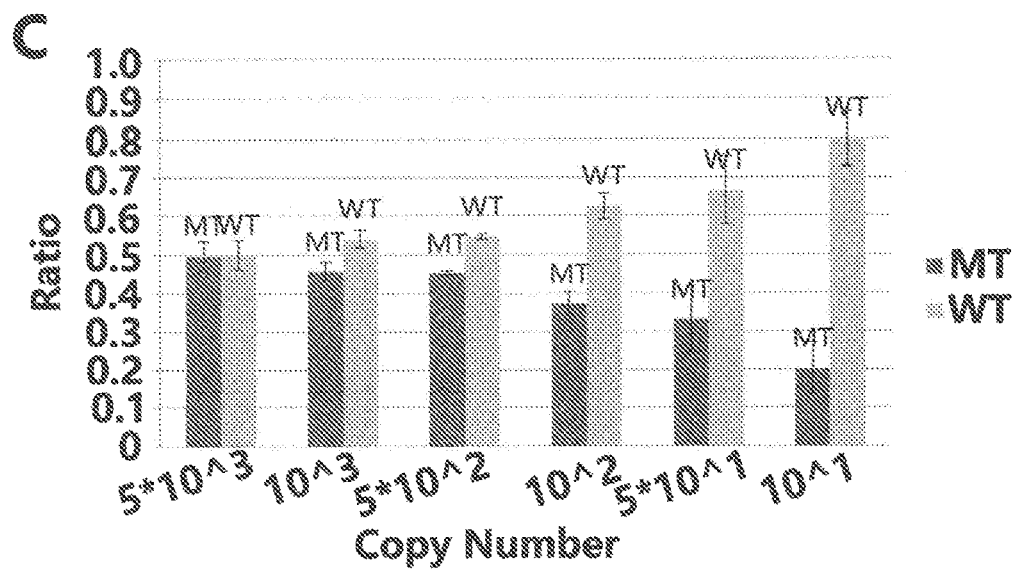
Figure 3:
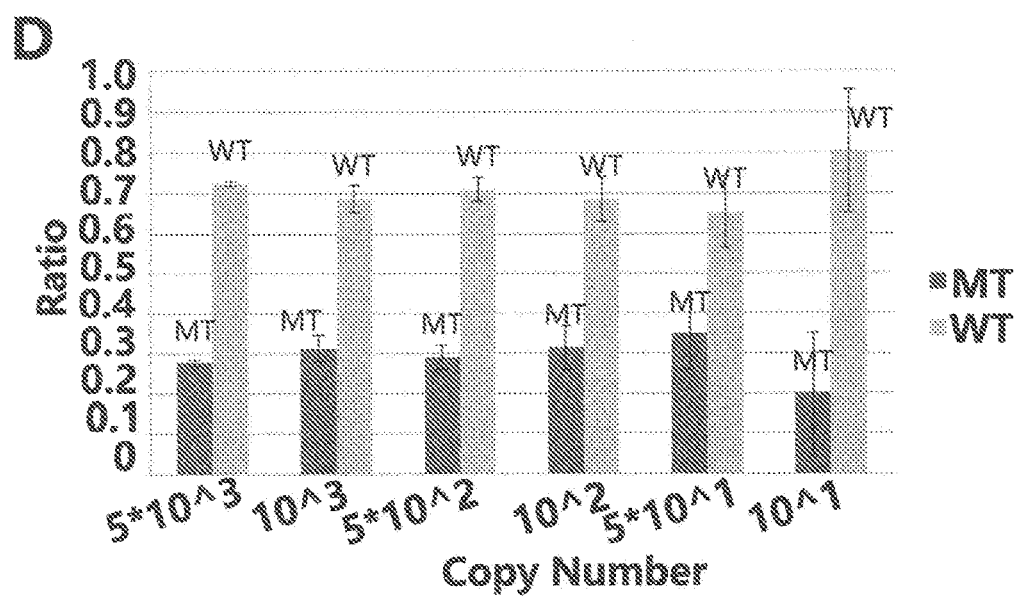
Figure 3:
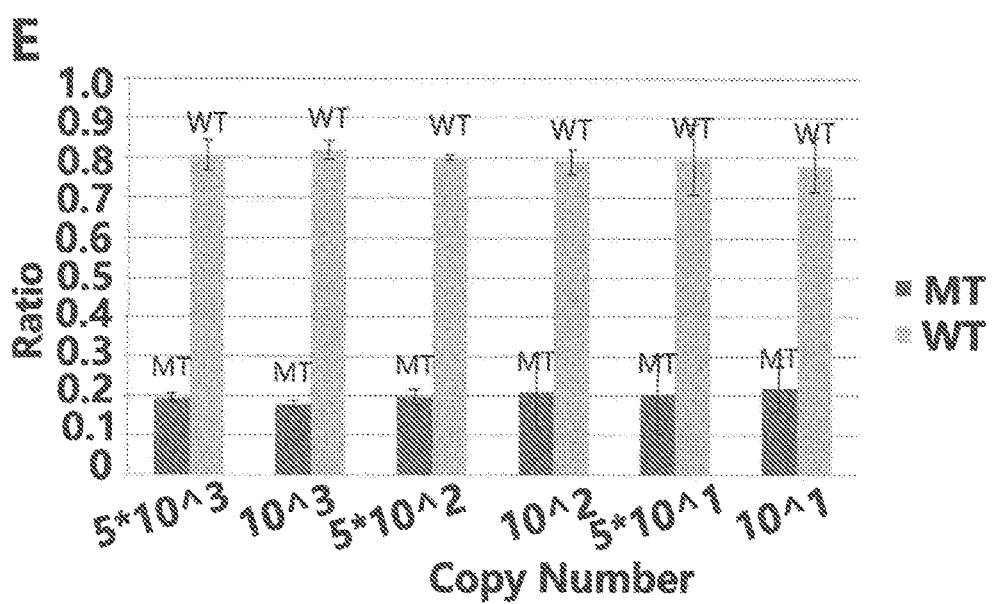
Figure 4:
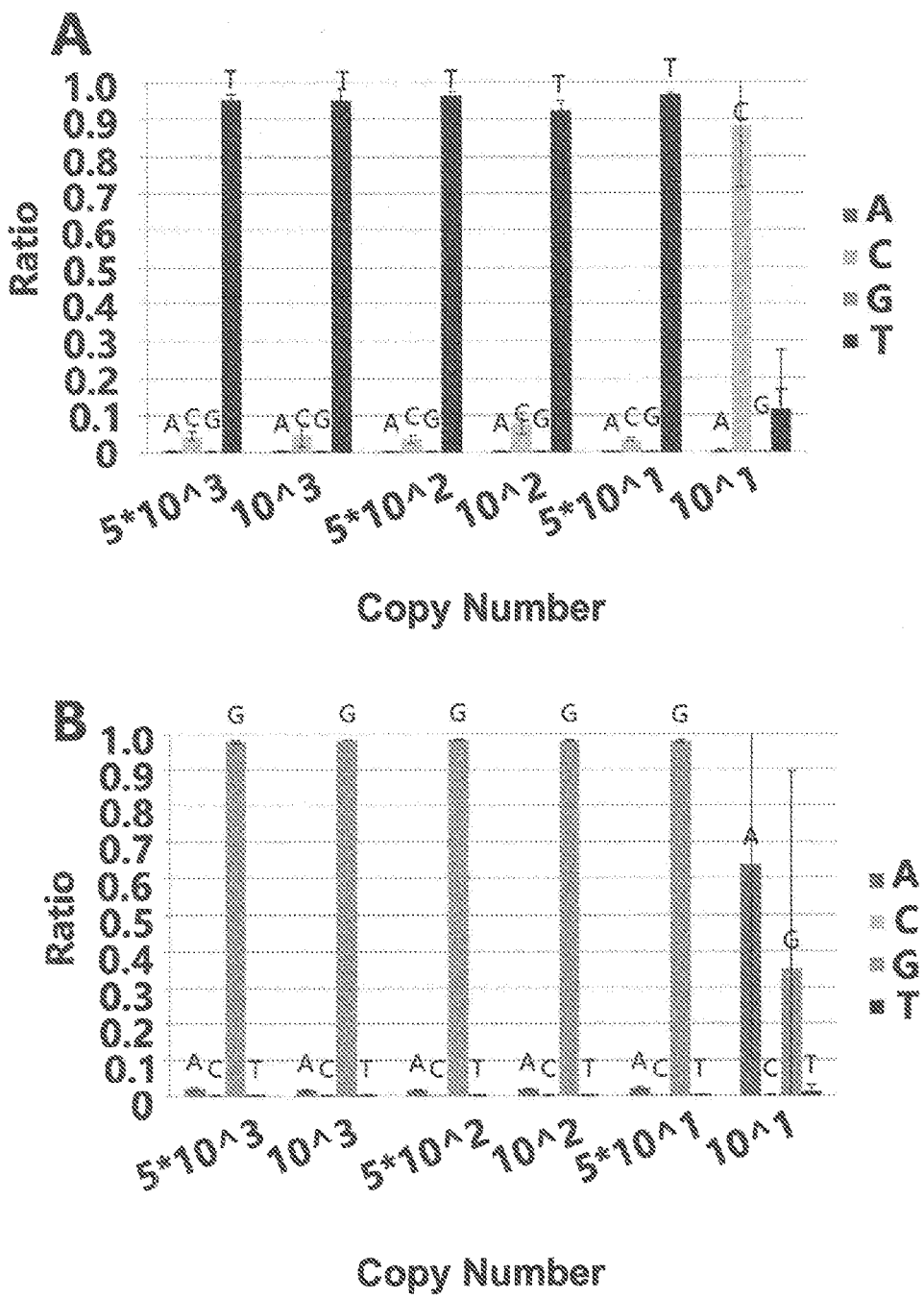
FIGS. 4A-4E are the testing results of plasmid group III.
Figure 4:
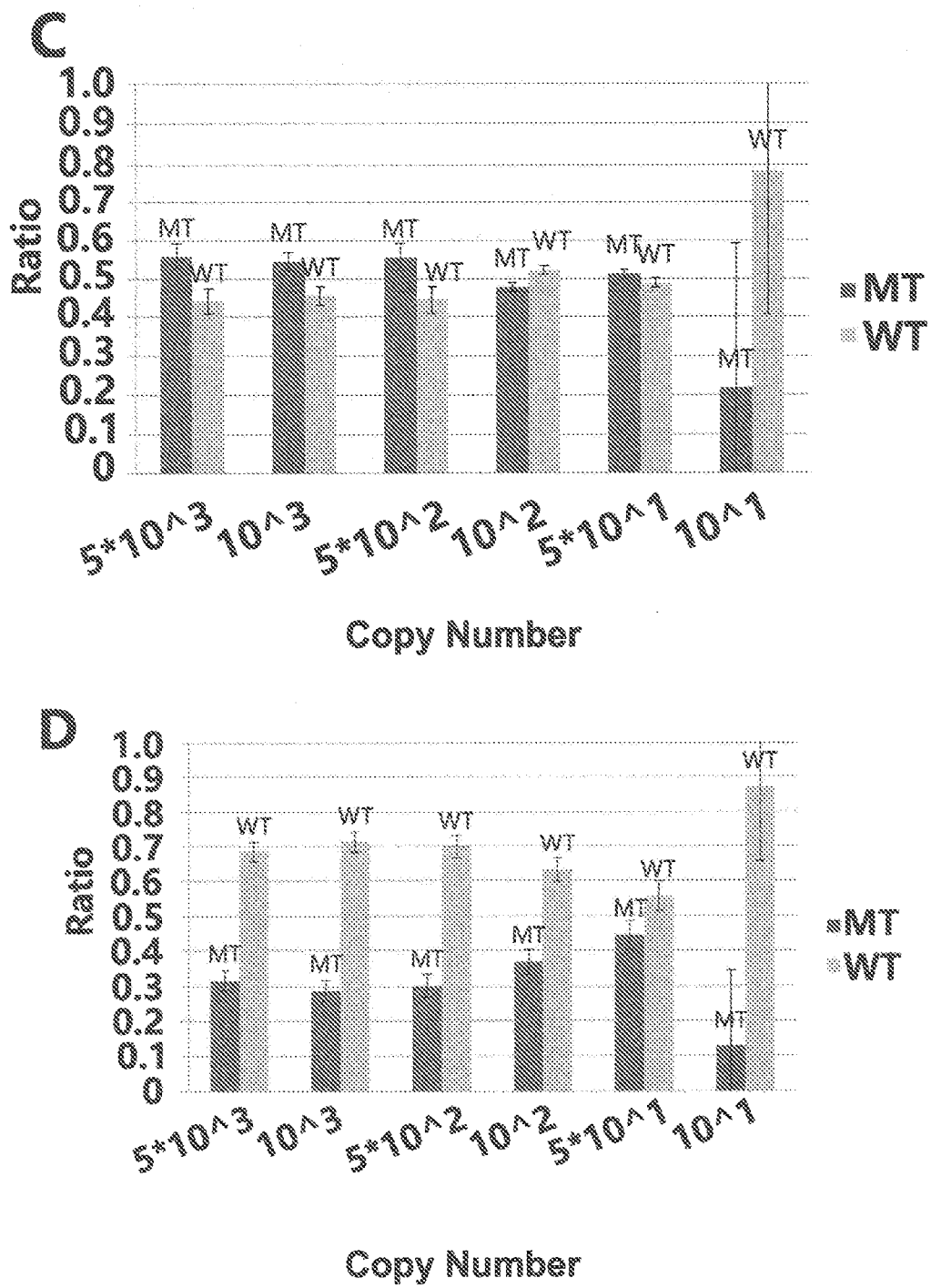
Figure 4:
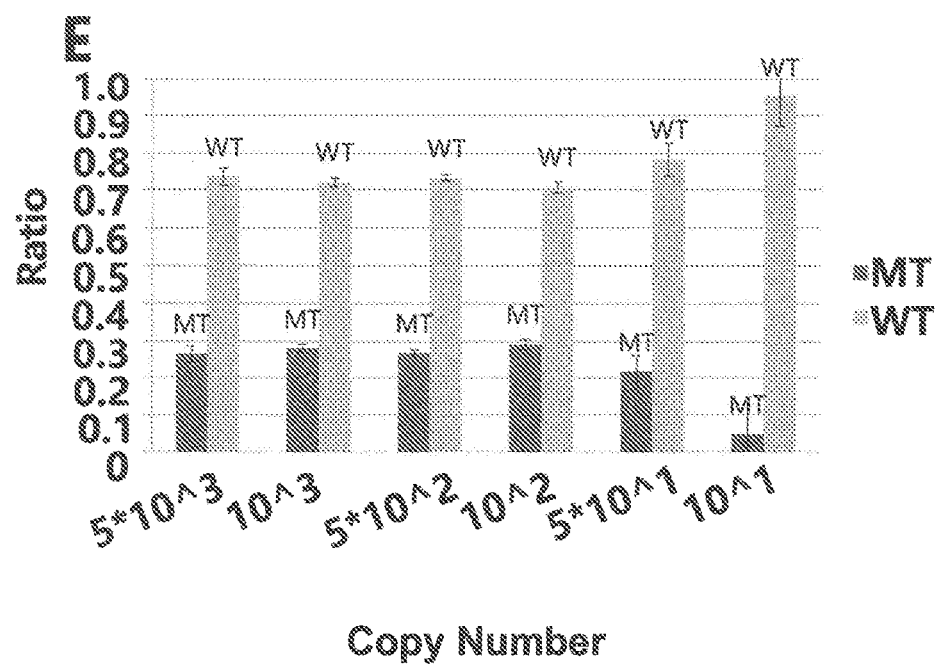

Experimental results showed that using the methods disclosed herein, for plasmid group I (in which the 1494 site, IVS7-2 site, 176 site, 235 site, and 299 site were all wild-type), the sensibility was $5\times10^1$ copy (FIG. 2); for plasmid group II (in which the 1494 sites were all mutant, 50% of the IVS7-2 sites were mutant, 25% of the 176 sites, 235 sites, or 299 sites were mutant), the sensibility of the 1494 sites and the IVS7-2 sites was $10^1$ copy, the sensibility of the 176 sites, 235 sites, or 299 sites was $4\times10^1$ copy (FIG. 3); for plasmid group III (the IVS7-2 sites and the 1494 sites were all mutant, 33.3% of the 235 sites, 176 sites, and 299 sites were mutant), the sensibility of the 1494 sites and the IVS7-2 sites was $5\times10^1$ copy, the sensibility of the 176 sites, the 235 sites, or the 299 sites was $3\times10^1$ copy (FIG. 4).

Example 2

Detection of SNP Based on High-Throughput Sequencing Technology in Human Genomic DNA Samples Probe and Pre-Amplification Primer Design 1. Test Sample Preparation Deafness patients' blood genomic DNA (verified homozygous mutant genomic DNA at the 235 residue of the GJB2 gene) and normal human blood genomic DNA (wild-type genomic DNA) were used, and each sample was repeated for three times. The concentration of nucleic acid was 10 ng/µL.

2. Probe and Pre-Amplification Primer Design

1) Probe Design

The principle of design is the same as in Example 1. The sequences of the probes are listed in Table 5.

TABLE 5

Probes.

| | | |
|---|---|---|
| 176WU-2 (SEQ ID No.: 12) | ACACGACGCTCTTCCGATCTCCAGGCTGCAAGAACGTGTG | 176/ASO/wild-type(WT) |
| 176MU-2 (SEQ ID No.: 13) | ACACGACGCTCTTCCGATCTTGCAACACCCTGCAGCCAG | 176/ASO/ Deletion Type (MT) |

TABLE 5-continued

Probes.

| | | |
|---|---|---|
| 176DP | CTACGATCACTACTTCCCCAGATCGGAAGAGCACACGTCT (SEQ ID NO: 14) | 176/LSO |
| 235WU | ACACGACGCTCTTCCGATCTACATCCGGCTATGGGCC (SEQ ID NO: 15) | 235/ASO/ WT |
| 235MU | ACACGACGCTCTTCCGATCTCACATCCGGCTATGGGC (SEQ ID NO: 16) | 235/ASO/ MT |
| 235DP | CTGCAGCTGATCTTCGTGTCGATCGGAAGAGCACACGTCT (SEQ ID NO: 17) | 235/LSO |
| 299WU | ACACGACGCTCTTCCGATCTTGGCCTACCGGAGACAT (SEQ ID NO: 18) | 235/ASO/ WT |
| 299MU | ACACGACGCTCTTCCGATCTCGTGGCCTACCGGAGAC (SEQ ID NO: 19) | 299/ASO/ MT |
| 299DP | GAGAAGAAGAGGAAGTTCATGATCGGAAGAGCACACGTCT (SEQ ID NO: 20) | 299/LSO |

2). Probe and Pre-Amplification Primer Design

The principle of design is the same as in Example 1. The primers used were GJB234F1/GJB234R1-B.

Pre-amplification, hybridization, ligation, amplification, and data analysis were performed substantially the same as in Example 1.

Figure 5:
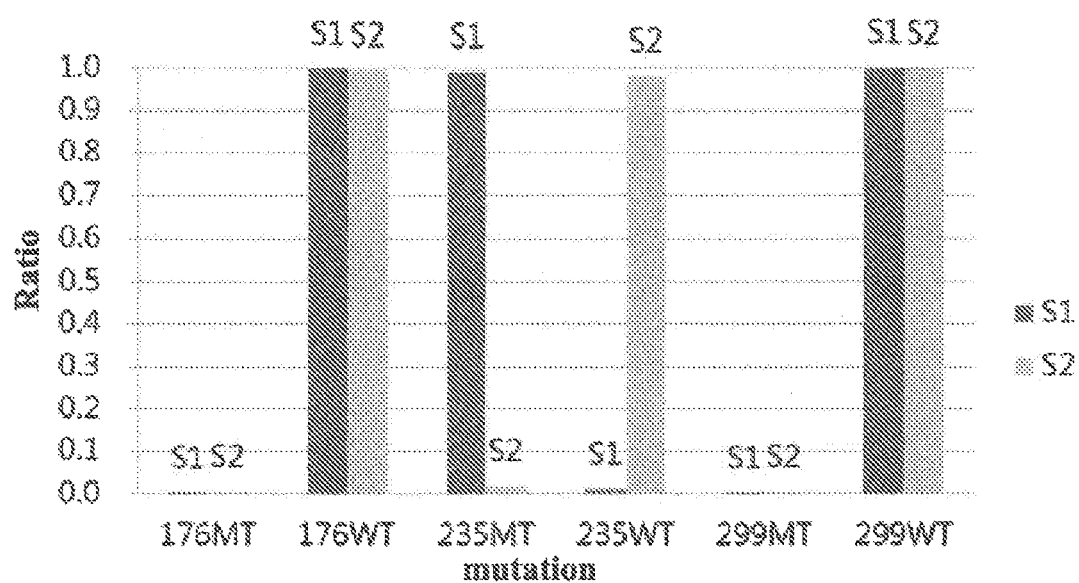
FIG. 5 is the testing result of 235 wild type genomic DNA and 235delC homozygous mutant genomic DNA.

Results are shown in FIG. 5. The genomic DNA of deafness patient was homozygous mutation at position 235, wild-type at position 176, and wild-type at position 299. The results were consistent with the sample setup.

The invention claimed is:

1. A probe set for analyzing a genetic locus of a target polynucleotide sequence, comprising:

one or more first probes comprising: (1) a first hybridization sequence that specifically binds to the target polynucleotide sequence upstream of or including the genetic locus, and (2) a first primer sequence upstream of the first hybridization sequence, wherein the first primer sequence does not bind to the target polynucleotide sequence; and one or more second probes comprising: (i) a second hybridization sequence that specifically binds to the target polynucleotide sequence downstream of or starting from the genetic locus, and (ii) a second primer sequence downstream of the second hybridization sequence, wherein the second primer sequence does not bind to the target polynucleotide sequence, wherein:

the extension directions of the first and second probes are the same;

the first probe is upstream of the second probe; and the first and second probes are adjacent and, when coupled, form a sequence comprising the genetic locus, and wherein:

a) the genetic locus comprises an insertion at the $n^{th}$ residue of a wild-type target polynucleotide sequence; and the one or more first probes comprise at least two first probes, one of which specifically binds to the wild-type target polynucleotide sequence until and excluding the $n^{th}$ residue, while the other specifically binds to the target polynucleotide sequence including and until the last residue of the inserted sequence, and the second hybridization sequence of the one or more second probes specifically binds to the target polynucleotide sequence downstream of the insertion, and the 5' terminal nucleotide of the one or more second probes is complementary to $n^{th}$ residue; or the one or more second probes comprise at least two second probes, one of which specifically binds to the wild-type target polynucleotide sequence starting from the $n^{th}$ residue, while the other specifically binds to the target polynucleotide sequence including and from the first residue of the inserted sequence, and the first hybridization sequence of the one or more first probes specifically binds to the target polynucleotide sequence upstream of the insertion, and the 3' terminal nucleotide of the one or more first probes is complementary to the residue immediately upstream of $n^{th}$ residue in the wild-type target polynucleotide; or b) the genetic locus comprises a deletion at the $n^{th}$ residue of a wild-type target polynucleotide sequence; and the one or more first probes comprise at least two first probes, one of which specifically binds to the wild-type target polynucleotide sequence until and excluding the $n^{th}$ residue, while the other specifically binds to the target polynucleotide sequence until the first residue immediately upstream of the deleted sequence, and the second hybridization sequence of the one or more second probes specifically binds to the target polynucleotide sequence downstream of the deletion, and the 5' terminal nucleotide of the one or more second probes is complementary to $n^{th}$ residue; or the one or more second probes comprise at least two second probes, one of which specifically binds to the wild-type target polynucleotide sequence starting from the $n^{th}$ residue, while the other specifically binds to the target polynucleotide sequence including and from the first residue of the deleted sequence, and the first hybridization sequence of the one or more first probes specifically binds to the target polynucleotide sequence upstream of the deletion, and the 5' terminal nucleotide of the one or more first probes is complementary to the residue immediately upstream of $n^{th}$ residue in the wild-type target polynucleotide.

2. The probe set of claim 1, wherein:
the genetic locus comprises an SNP or a point mutation; and the first hybridization sequence of the one or more first probes specifically binds to the target polynucleotide sequence including the SNP or point mutation, and the 3' terminal nucleotide of the one or more first probes is complementary to the nucleotide at the SNP or point mutation locus, and the second hybridization sequence of the one or more second probes specifically binds to the target polynucleotide sequence downstream of the SNP or point mutation, and the 5' terminal nucleotide of the one or more second probes is complementary to the nucleotide immediately downstream of the SNP or point mutant locus; or the first hybridization sequence of the one or more first probes specifically binds to the target polynucleotide sequence upstream of the SNP or point mutation, and the 3' terminal nucleotide of the one or more first probes is complementary to the nucleotide immediately upstream of the SNP or point mutation locus, and the second hybridization sequence of the one or more second probes specifically binds to the target polynucleotide sequence starting from the SNP or point mutation, and the 5' terminal nucleotide of the one or more second probes is complementary to the nucleotide at the SNP or point mutation locus.

3. The probe set of claim 2, wherein the first primer sequence of the one or more first probes is unique for the residue at the SNP or mutant locus.

4. The probe set of claim 1, wherein the 5' terminus of the one or more second probes is phosphorylated.

5. The probe set of claim 1, wherein the first primer sequence of the one or more first probes is a universal primer sequence.

6. The probe set of claim 1, wherein the second primer sequence of the one or more second probes is a universal primer sequence.

7. The probe set of claim 1, wherein:
the genetic locus comprises an insertion at the $n^{th}$ residue of a wild-type target polynucleotide sequence; and the one or more first probes comprise at least two first probes, one of which specifically binds to the wild-type target polynucleotide sequence until and excluding the $n^{th}$ residue, while the other specifically binds to the target polynucleotide sequence including and until the last residue of the inserted sequence, and the second hybridization sequence of the one or more second probes specifically binds to the target polynucleotide sequence downstream of the insertion, and the 5' terminal nucleotide of the one or more second probes is complementary to $n^{th}$ residue; or the one or more second probes comprise at least two second probes, one of which specifically binds to the wild-type target polynucleotide sequence starting from the $n^{th}$ residue, while the other specifically binds to the target polynucleotide sequence including and from the first residue of the inserted sequence, and the first hybridization sequence of the one or more first probes specifically binds to the target polynucleotide sequence upstream of the insertion, and the 3' terminal nucleotide of the one or more first probes is complementary to the residue immediately upstream of $n^{th}$ residue in the wild-type target polynucleotide.

8. The probe set of claim 7, wherein the first primer sequence of the one or more first probes is a universal primer sequence.

9. The probe set of claim 7, wherein the two first probes comprise different first primer sequences.

10. The probe set of claim 7, wherein the 5' terminus of the one or more second probes is phosphorylated.

11. The probe set of claim 7, wherein the second primer sequence of the one or more second probes is a universal primer sequence.

12. The probe set of claim 1, wherein:
the genetic locus comprises a deletion at the $n^{th}$ residue of a wild-type target polynucleotide sequence;

the one or more first probes comprise at least two first probes, one of which specifically binds to the wild-type target polynucleotide sequence until and excluding the $n^{th}$ residue, while the other specifically binds to the target polynucleotide sequence until the first residue immediately upstream of the deleted sequence, and the second hybridization sequence of the one or more second probes specifically binds to the target polynucleotide sequence downstream of the deletion, and the 5' terminal nucleotide of the one or more second probes is complementary to $n^{th}$ residue; or the one or more second probes comprise at least two second probes, one of which specifically binds to the wild-type target polynucleotide sequence starting from the $n^{th}$ residue, while the other specifically binds to the target polynucleotide sequence including and from the first residue of the deleted sequence, and the first hybridization sequence of the one or more first probes specifically binds to the target polynucleotide sequence upstream of the deletion, and the 5' terminal nucleotide of the one or more first probes is complementary to the residue immediately upstream of n$^{th}$ residue in the wild-type target polynucleotide.

13. The probe set of claim 1, wherein the genetic locus is in a deafness related gene.

14. The probe set of claim 13, wherein the one or more first probes for 1494C>T comprises the polynucleotide sequence set forth in SEQ ID NO: 21, SEQ ID NO: 22, SEQ ID NO: 23, and/or SEQ ID NO: 24.

15. The probe set of claim 13, wherein the one or more second probes for 1494C>T comprises the polynucleotide sequence set forth in SEQ ID NO: 25.

16. The probe set of claim 13, wherein the one or more first probes for IVS7-2A>G comprises the polynucleotide sequence set forth in SEQ ID NO: 7, SEQ ID NO: 8, SEQ ID NO: 9, and/or SEQ ID NO: 10.

17. The probe set of claim 13, wherein the one or more second probes for IVS7-2A>G comprises the polynucleotide sequence set forth in SEQ ID NO: 11.

18. The probe set of claim 13, wherein the one or more first probes for 235delC comprises the polynucleotide sequence set forth in SEQ ID NO: 15 and/or SEQ ID NO:16.

19. The probe set of claim 13, wherein the one or more second probes for 235delC comprises the polynucleotide sequence set forth in SEQ ID NO: 17.

20. The probe set of claim 13, wherein the one or more first probes for 176DEL16 comprises the polynucleotide sequence set forth in SEQ ID NO: 12 and/or SEQ ID NO:13.

21. The probe set of claim 13, wherein the one or more second probes for 176DEL16 comprises the polynucleotide sequence set forth in SEQ ID NO: 14.

22. The probe set of claim 13, wherein the one or more first probes for 299delAT comprises the polynucleotide sequence set forth in SEQ ID NO: 18 and/or SEQ ID NO:19.

23. The probe set of claim 13, wherein the one or more second probes for 299delAT comprises the polynucleotide sequence set forth in SEQ ID NO: 20.

24. The probe set of claim 13, wherein the deafness related gene is GJB2, SLC26A4, or 12SrRNA.

25. The probe set of claim 24, wherein the genetic locus comprises 1494C>T, IVS7-2A>G, 235delC, 176DEL16, and/or 299delAT.

26. A kit for analyzing a genetic locus, comprising the probe set of claim 1.

27. The kit of claim 26, further comprising a primer pair for amplifying 176del16, 299delAT, and/or 235delC.

28. The kit of claim 27, wherein the primer pair for amplifying 176del16, 299delAT, and/or 235delC comprises the polynucleotide sequences set forth in SEQ ID NO: 28 and SEQ ID NO:29.

29. The kit of claim 26, further comprising a primer pair for amplifying 1494C>T.

30. The kit of claim 29, wherein the primer pair for amplifying 1494C>T comprises the polynucleotide sequences set forth in SEQ ID NO: 26 and SEQ ID NO: 27.

31. The kit of claim 26, further comprising a primer pair for amplifying IVS7-2A>G.

32. The kit of claim 31, wherein the primer pair for amplifying IVS7-2A>G comprises the polynucleotide sequences set forth in SEQ ID NO: 30 and SEQ ID NO: 31.

33. The kit of claim 26, wherein one or both of the primers of the primer pair are labeled.

34. The kit of claim 33, wherein the label comprises biotin.

35. The kit of claim 26, further comprising a barcode specific primer and/or a common primer.

36. The kit of claim 35, wherein the barcode specific primer comprises the polynucleotide sequences set forth in SEQ ID NO: 32, and the common primer comprises the polynucleotide sequences set forth in SEQ ID NO: 33.

37. A composition for analyzing at least a first genetic locus and a second genetic locus, comprising a first probe set of claim 1 for the first genetic locus, and a second probe set of claim 1 for the second genetic locus.

38. The composition of claim 37, wherein the probes in the first probe set are in equal molar amount, and the probes in the second probe set are in equal molar amount.

39. The composition of claim 37, wherein the first genetic locus comprises an SNP or point mutation, and the second genetic locus comprises a deletion and/or insertion.

40. The composition of claim 39, wherein the SNP or point mutation comprises 1494C>T, and/or IVS7-2A>G, and the deletion and/or insertion comprise 235delC, 176DEL16, and/or 299delAT.

41. The composition of claim 37, wherein the first and second probe sets comprise at least two of the following probe sets:
(1) a first probe comprising the polynucleotide sequences set forth in SEQ ID NO: 25, and one or more of a second probe comprising the polynucleotide sequences set forth in SEQ ID NO: 21, SEQ ID NO: 22, SEQ ID NO: 23, or SEQ ID NO: 24;
(2) a first probe comprising the polynucleotide sequences set forth in SEQ ID NO: 11, and one or more of a second probe comprising the polynucleotide sequences set forth in SEQ ID NO: 7, SEQ ID NO: 8, SEQ ID NO: 9, or SEQ ID NO: 10;
(3) a first probe comprising the polynucleotide sequences set forth in SEQ ID NO: 17, and one or more of a second probe comprising the polynucleotide sequences set forth in SEQ ID NO: 15 or SEQ ID NO: 16;
(4) a first probe comprising the polynucleotide sequences set forth in SEQ ID NO: 14, and one or more of a second probe comprising the polynucleotide sequences set forth in SEQ ID NO: 12 or SEQ ID NO: 13; and
(5) a first probe comprising the polynucleotide sequences set forth in SEQ ID NO: 20, and one or more of a second probe comprising the polynucleotide sequences set forth in SEQ ID NO: 18 or SEQ ID NO: 19.

* * * * *